US006150588A

United States Patent [19]

[11] Patent Number: 6,150,588

[45] Date of Patent: Nov. 21, 2000

Attenborough et al.

[54] DNA ENCODING ANTIMICROBIAL PROTEINS FROM IMPATIENS

[75] Inventors: Sheila Attenborough, Maidenhead, United Kingdom; Willem Frans Broekaert, Dilbeek, Belgium; Rupert William Osborn, Twickenham, United Kingdom; John Anthony Ray, Bracknell, United Kingdom; Sarah Bronwen Rees, Bracknell, United Kingdom; Ravindra Haribhai Tailor, Bracknell, United Kingdom

[73] Assignee: Zeneca Limited, London, United Kingdom

[21] Appl. No.: 08/831,028

[22] Filed: Apr. 4, 1997

Related U.S. Application Data

[62] Division of application No. 08/700,442, filed as application No. PCT/GB95/00509, Mar. 9, 1995, Pat. No. 5,861,480.

[30] Foreign Application Priority Data

Mar. 11, 1994 [GB] United Kingdom ................... 9404807

[51] Int. Cl.[7] ............................... A01H 5/00; C12N 1/21; C12N 15/29

[52] U.S. Cl. ........................ 800/298; 435/252.3; 536/23.6

[58] Field of Search .......................... 536/23.6; 435/69.1, 435/320.1, 419, 468, 243, 252.3; 800/279, 301, 298

[56] References Cited

U.S. PATENT DOCUMENTS 5,162,601 11/1992 Slightom ................................ 800/205
5,597,945 1/1997 Jaynes et al. ........................... 800/205

FOREIGN PATENT DOCUMENTS

WO 92/21699 12/1992 WIPO .

OTHER PUBLICATIONS

Stam M, et al. "The silence of genes in transgenic plants." Ann. Bot. 79: 3–12, 1997.

Koziel MG, et al. "Optimizing expression of transgenes with an emphasis on post–transcriptional events." Plant Mol. Biol. 32: 393–405, 1996.

Smith CJS, et al. "Antisense RNA inhibition of polygalacturonase gene expression in transgenic tomatoes." Nature 334: 724–726, Aug. 25, 1988.

Reddy, V.K. et al., Pesticides (Bombay), vol. 21, No. 1, pp. 17–18, 1987.

Thompson, M.A., J. Alabama Acad. Sci., vol. 62, nos. 2–3, p. 89, 1991.

Cammue, B.P. et al., CIBA Foundation Symposium No. 186, Jan. 18–20, 1994, pp. 91–106.

Marcos, F.J. et al., Plant Molecular Biology, vol. 24, No. 3, pp. 495–503, Feb. 1994.

Timon–David, P. et al., Biological Abstracts, vol. 73, Abstract No. 8375, Philadelphia, PA, U.S., 1982.

Santos, Filho, D.D., Biological Abstracts, vol. 92, Abstract No. 108986, Philadelphia, PA, U.S., 1991.

*Primary Examiner*—Amy J. Nelson
*Attorney, Agent, or Firm*—Liza D. Hohenschutz

[57] ABSTRACT

Antimicrobial proteins are isolated from seeds of Impatiens, and show a wide range of antifungal activity and some antibacterial activity. DNA encoding the proteins is isolated and incorporated into vectors. Plants transformed with this DNA are produced. The invention further provides a method of expressing polyproteins in transgenic plants using DNA constructs based on the structure of the gene encoding the Impatiens antimicrobial proteins.

6 Claims, 13 Drawing Sheets

```
Ib-AMP1     ? ? G R R C C G W G P G R R Y C V R W C
                <----Ib1C1----->
                    <--------------------Ib1T1----------->

Ib-AMP2         G R R C C N W G P G R R Y C K R W C
                <----Ib2C1----->
                              <----Ib2C2---->
                                           <--Ib2C3-->

Ib-AMP3                       G P G R K Y C K R W C
                              <----Ib3C1--->
                                           <--Ib3C2-->

Ib-AMP4         G R R C C G W G P G R R Y C R R W C
                <-----Ib4C1---->
                             <----Ib4C2---->
                                           <--Ib4C3-->
```

```
              10                      21              30              39               48              57
 ATTTTTAGGT GAGGAAAA ATG GTC CAA AAA GGT GTA GTC TTT GGG GTG CTC CTA ATT
                     M   V   Q   K   G   V   V   F   G   V   L   L   I

             66      75      84          93      102         111
 CTC TTC ATC TGC TCT ACG CTC ACT TCG GCC GAT TCG AAG CCA AAC CCT ACG AAA
 L   F   I   C   S   T   L   T   S   A   D   S   K   P   N   P   T   K

             120     129     138         147     156         165
 GAG GAA GAA CCA GCG AAG AAA CCG GAT GAG GTC AGC GTA AAG AGC GGT GGA CCG
 E   E   E   P   A   K   K   P   D   E   V   S   V   K   S   G   G   P

             174     183     192         201     210         219
 GAG GTG TCG GAG GAT CAA TAC CGT CAT CGG TGC TGC GCT TGG GGA CCT GGG CGA
 E   V   S   E   D   Q   Y   R   H   R   C   C   A   W   G   P   G   R

             228     237     246         255     264         273
 AAA TAT TGC AAG CGG TGG TGT GCT AAC GCT GAA GAG GCG GCG GCC GCA ATC CCC
 K   Y   C   K   R   W   C   A   N   A   E   E   A   A   A   A   I   P

             282     291     300         309     318         327
 GAG GCA AGT GAA GAA TTA GCT CAG GAG GAG GCT CCG GTG TAC TCG GAG GAT CAG
 E   A   S   E   E   L   A   Q   E   R   A   P   V   Y   S   E   D   Q

             336     345     354         363     372         381
 TGG GGT CGT CGG TGC TGC GGC TGG GGA CCC GGC CGA AGA TAC TGC GTG CGC TGG
 W   G   R   R   C   C   G   W   G   P   G   R   R   Y   C   V   R   W

             390     399     408         417     426         435
 TGT CAA AAC GCG GAA GAG GCG GCC GCG GCA ATC CCC GAG GCG ACT GAA AAA GCT
 C   Q   N   A   E   E   A   A   A   A   I   P   E   A   T   E   K   A

             444     453     462         471     480         489
 CAG GAG GCT CCG GTG TAC TCG GAG GAT CAG TGG GGT CGT CGA TGC TGC GGC TGG
 Q   E   A   P   V   Y   S   E   D   Q   W   G   R   R   C   C   G   W

             498     507     516         525     534         543
 GGA CCC GGC CGA CGG TAT TGC GTG CGC TGG TGT CAA AAC GCG GAA GAG GCG GCC
 G   P   G   R   R   Y   C   V   R   W   C   Q   N   A   E   E   A   A
```

FIG. 10(I)

```
        552         561         570         579         588         597
GCG GCG GTG GCA ATC CCC GAG GCA AGT GAG AAA GCT CAG GAG GGA CCC GTG TAC
A   A   V   A   I   P   E   A   S   E   K   A   0   E   G   P   V   Y

        606         615         624         633         642         651
TCG GAG GAT CAG TGG GGT CGC CGA TGC TGC GGT TGG GGA CCT GGC CGT AGG TAT
S   E   D   Q   W   G   R   R   C   C   G   W   G   P   G   R   R   Y

        660         669         678         687         696         705
TGC GTG CGG TGG TGC AGC AAC GCC GCC GAC GAG GTG GCA ACA CCC GAG GAC GTA
C   V   R   W   C   S   N   A   A   D   E   V   A   T   P   E   D   V

        714         723         732         741         750         759
GAA CCG GGT CAG TAC GGT CGT CGG TGC TGC AAC TGG GGA CCT GGG CGA AGG TAT
E   P   G   Q   Y   G   R   R   C   C   N   W   G   P   G   R   R   Y

        768         777         786         795         804         813
TGC AAG CGG TGG TGT CAT AAT GCG GCT GAA GAG GCA ACT CTC AAG GCA TTT GAA
C   K   R   W   C   H   N   A   A   E   E   A   T   L   K   A   F   E

        822         831         840         849         858         867
GAG GAA GCA GCT CGG GAG CAA CCG GTG TAC TCG GAG GAC CAG TGG GGT CGC CGG
E   E   A   A   R   E   Q   P   V   Y   S   E   D   Q   W   G   R   R

        876         885         894         903         912         921
TGC TGC GGT TGG GGA CCC GGC CGT AGG TAC TGC AGG CGG TGG TGT CAA AGC GCC
C   C   G   W   G   P   G   R   R   Y   C   R   R   W   C   Q   S   A

        930         939         948         957         966         975
GAA GAA GCG GCT GCG TTC CAG GCT GGG GAG GTA ACT GCT TCC TTG ATG CTC ATC
E   E   A   A   A   F   Q   A   G   E   V   T   A   S   L   M   L   I

        984         993        1002        1011        1020       1030
ATG TTT AAG GCA TGC CCA TGC ATG GGG CCG GTG CCT TCT GTT TAA GGCCACTCTA
M   F   K   A   C   P   C   M   G   P   V   P   S   V

      1040       1050       1060       1070       1080       1090       1100
GCTAGCTACG TACTCTTAAT AAGGGCACAT GAAAAAGTTT GTCCTTTAGA AATAAGGCAC AGTAAGAAAT
      1110       1120       1130       1140       1150       1160       1170
AAAATGTCCA ACTTCTTTTA TGAAAGAAGT GAACAATAAG TGTAAGCTGA ATAATATATA TTGTGACACG
      1180       1190       1200       1210       1220       1230
TTTGTTGTTG TACAAAAATA ACATCTTTTC AGATGAACAA CCTTTAATGG AAAAAAAAAA AAAAAAAA
```

FIG. 10(II)

IBAMP GENE IN pMJB1 VECTOR

Cloning of IBAMP gene into pUC based vector pMJB1

Plant Vector Construct with IBAMP gene

DNA ENCODING ANTIMICROBIAL PROTEINS FROM IMPATIENS

This application is a division of application Ser. No. 08/700,442 filed Aug. 19, 1996, now U.S. Pat. No. 5,861, 480, which is a 371 of PCT/GB95/00509 filed Mar. 9, 1995.

BACKGROUND OF THE INVENTION

This invention relates to antimicrobial proteins, processes for their manufacture and use, and DNA sequences encoding them. In particular it relates to antimicrobial proteins capable of being isolated from seeds of Aralia or Impatiens.

In this context, antimicrobial proteins are defined as proteins or peptides possessing at least one of the following activities: antifungal activity (which may include anti-yeast activity); antibacterial activity. Activity includes a range of antagonistic effects such as partial inhibition or death. Antimicrobial proteins may be oligomeric or may be single peptide units.

The genus Aralia is part of the Araliaceae, a medium-sized plant family whose best known members are ivy and ginseng. Medicinal extracts have been obtained from some Aralia species, such as *Aralia cordata.*

The genus Impatiens is part of the Balsaminaceae plant family. There are five hundred to six hundred Impatiens species, many of which are commercially cultivated as greenhouse or pot plants.

Plants produce a wide array of antifungal compounds to combat potential invaders and over the last ten years it has become clear that proteins with antifungal activity form an important part of these defences. Several classes of such proteins have been described including thionins, beta-1,3-glucanases, ribosome-inactivating proteins, zeamatins, chitin-binding lectins and chitinases. These proteins have gained considerable attention as they could potentially be used as biocontrol agents.

Antimicrobial proteins with activity against plant pathogenic fungi have been isolated from certain plant species. We have previously described the structural and antifungal properties of several such proteins, including:

Mj-AMP1 and Mj-AMP2 from *Mirabilis jalapa* seeds (Cammue BPA et al, 1992, J Biol Chem, 267:2228–2233; International Application Publication Number WO92/15691);

Ac-AMP1 and Ac-AMP2 from *Amaranthus caudatus* seeds (Broekaert WF et al, 1992, Biochemistry, 37:4308–4314; International Application Publication Number WO92/21699);

Ca-AMP1 from *Capsicum annuum*, Bm-AMP1 from *Briza maxima*, Da-AFP from Delphinium, Cr-AFP from Catapodium, Ba-AFP from Baptisia and Ml-AFP from Microsensis (International Patent Application Publication Number WO94/11511);

Rs-AFP1 and Rs-AFP2 from *Raphanus sativus* seeds (Terras FRG et al, 1992, J Biol Chem, 267:15301–13309) and related proteins such as Bn-AFP1 and Bn-AFP2 from *Brassica napus*, Br-AFP1 and Br-AFP2 from *Brassica rapa*, Sa-AFP1 and Sa-AFP2 from *Sinapis alba*, At-AFP1 from *Arabidopsis thaliana*, Dm-AMP1 and Dm-AMP2 from *Dahlia merckii*, Cb-AMP1 and Cb-AMP2 from *Cnicus benedictus*, Lc-AMP from *Lathyrus cicera*, Ct-AMP1 and Ct-AMP2 from *Clitoria ternatea*, Rs-nsLTP from *Raphanus sativus* (International Patent Application Publication Number WO93/05153).

These and other plant-derived antimicrobial proteins are useful as fungicides or antibiotics, particularly for agricultural purposes. The proteins may be applied to or around a plant or may be expressed within a plant.

SUMMARY OF THE INVENTION

We have now purified new potent antimicrobial proteins.

According to the present invention, there is provided an antimicrobial protein of about 3 kDa, capable of being isolated from seeds of Aralia or Impatiens.

We have purified two new antimicrobial proteins from seeds of *Aralia chinensis*, hereafter called Arc-AMP1 (*Aralia chinensis*—antimicrobial protein 1) and Arc-AMP2 (*Aralia chinensis*—antimicrobial protein 2).

We have also purified four new antimicrobial proteins from seeds of *Impatiens balsamina*, hereafter called Ib-AMP1 (*Impatiens balsamina*—antimicrobial protein 1), Ib-AMP2 (*Impatiens balsamina*—antimicrobial protein 2), Ib-AMP3 (*Impatiens balsamina*—antimicrobial protein 3) and Ib-AMP4 (*Impatiens balsamina*—antimicrobial protein 4).

BRIEF DESCRIPTION OF THE DRAWINGS

FIG. 9 shows the amino acid sequences of peptide fragments of the Ib-AMPs.

FIGS. 10(I) and 10(II) show the sequence of the Ib-AMP cDNA and the encoded protein;

DETAILED DESCRIPTION OF THE INVENTION

Figure 1:
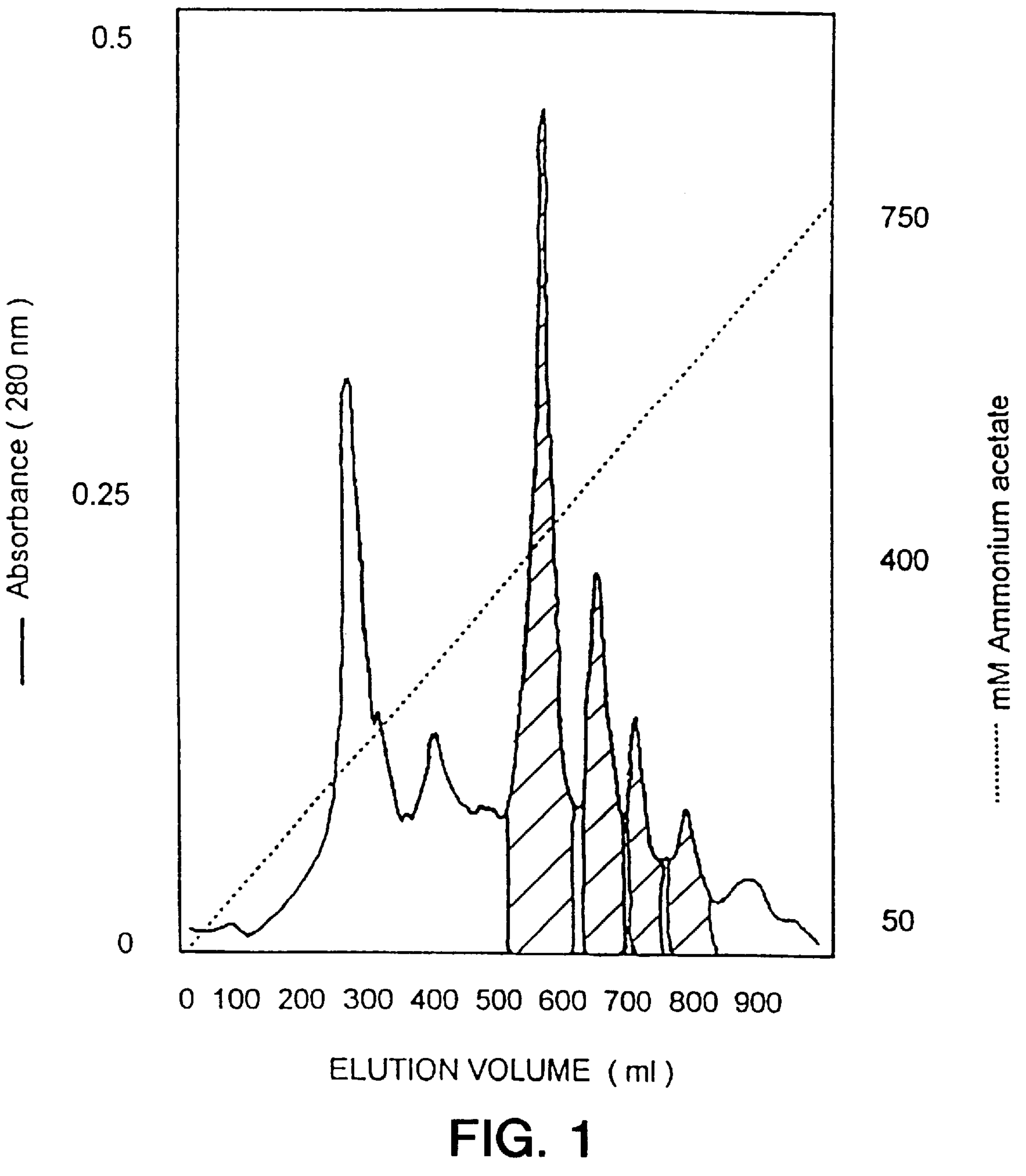
FIG. 1 shows the cation exchange chromatogram for purification of the Ib-AMPs.
Figure 2:
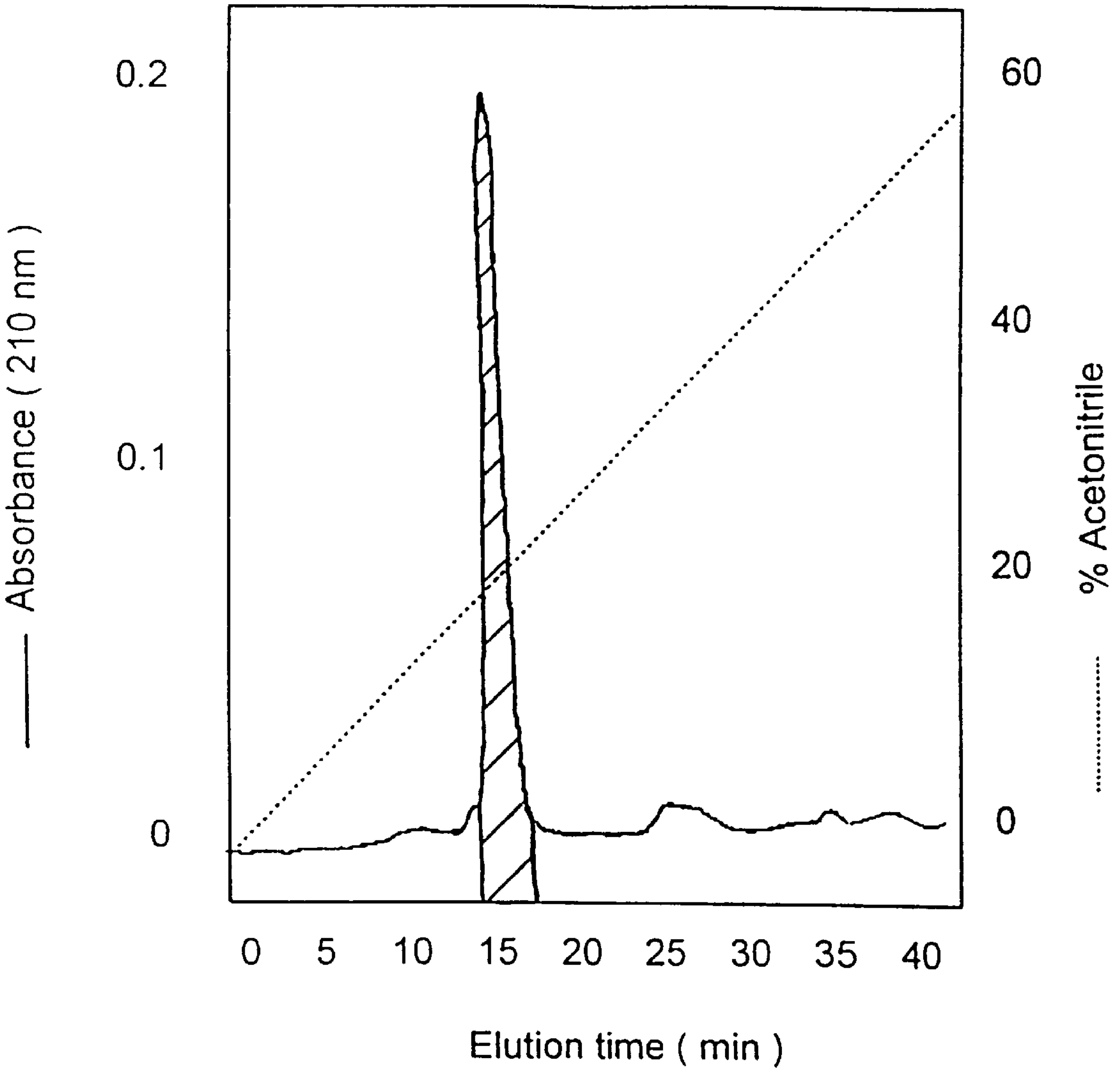
FIG. 2 shows the reversed phase chromatogram for purified Ib-AMP1.
Figure 3:
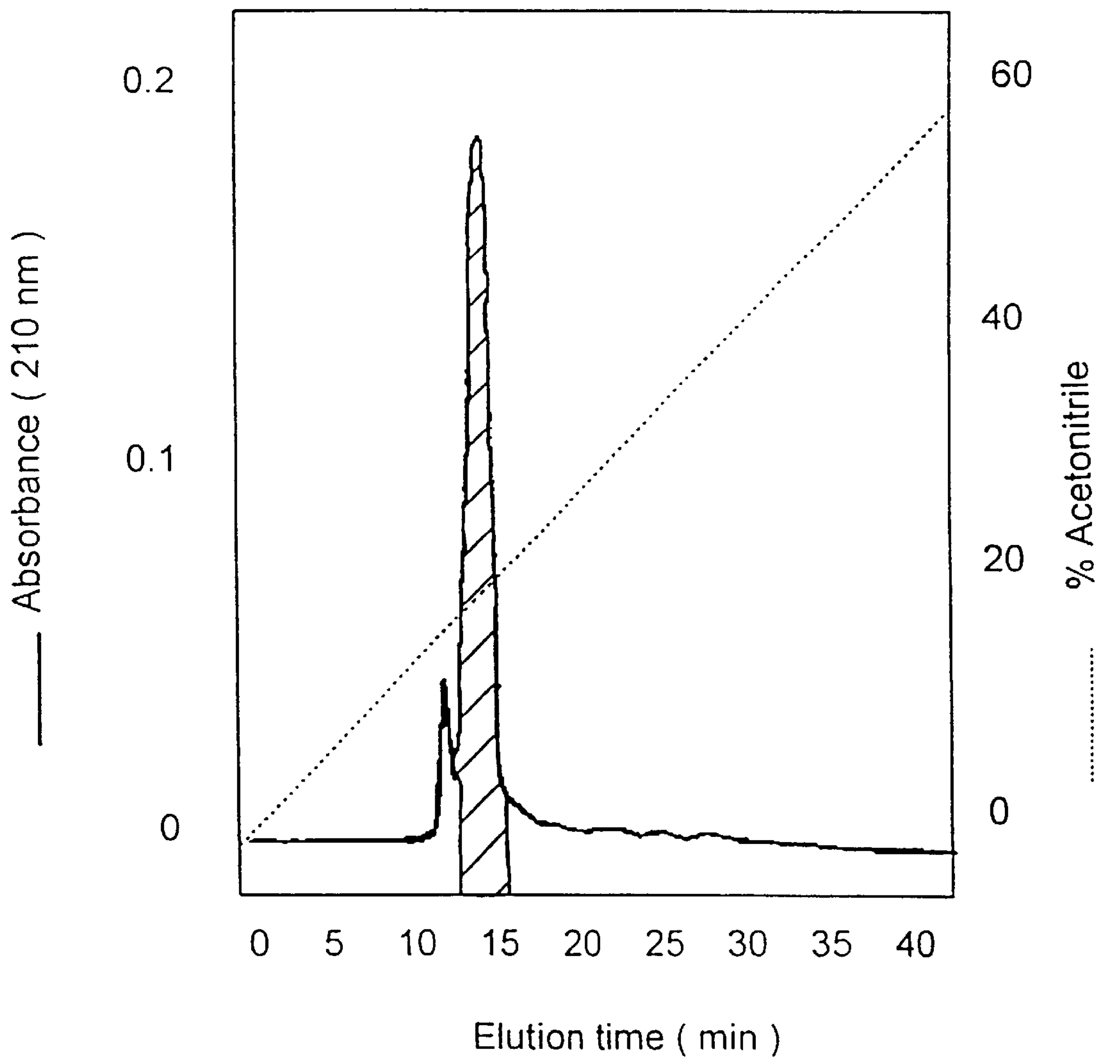
FIG. 3 shows the reversed phase chromatogram for purified Ib-AMP2.
Figure 4:
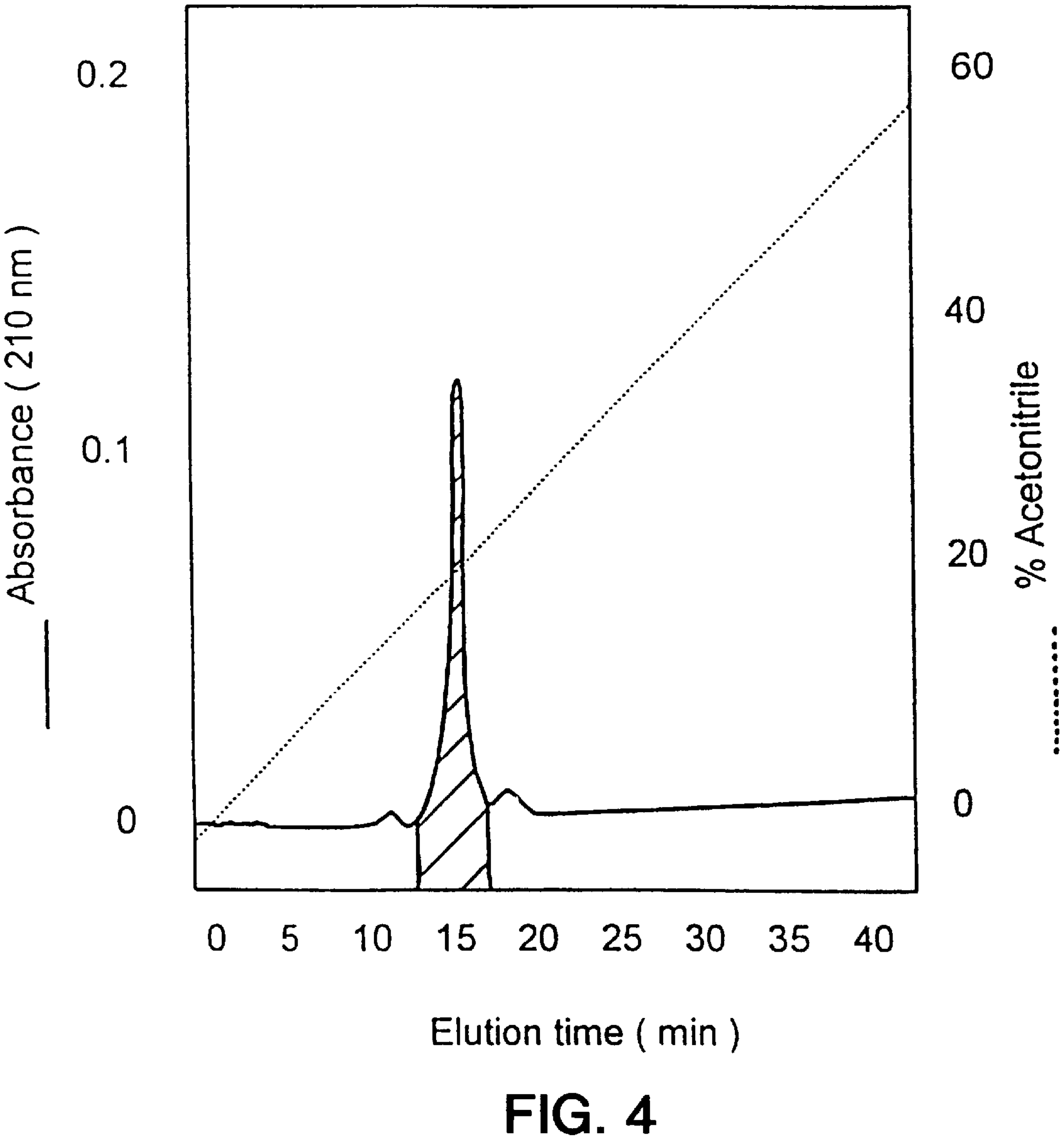
FIG. 4 shows the reversed phase chromatogram for purified Ib-AMP3.
Figure 5:
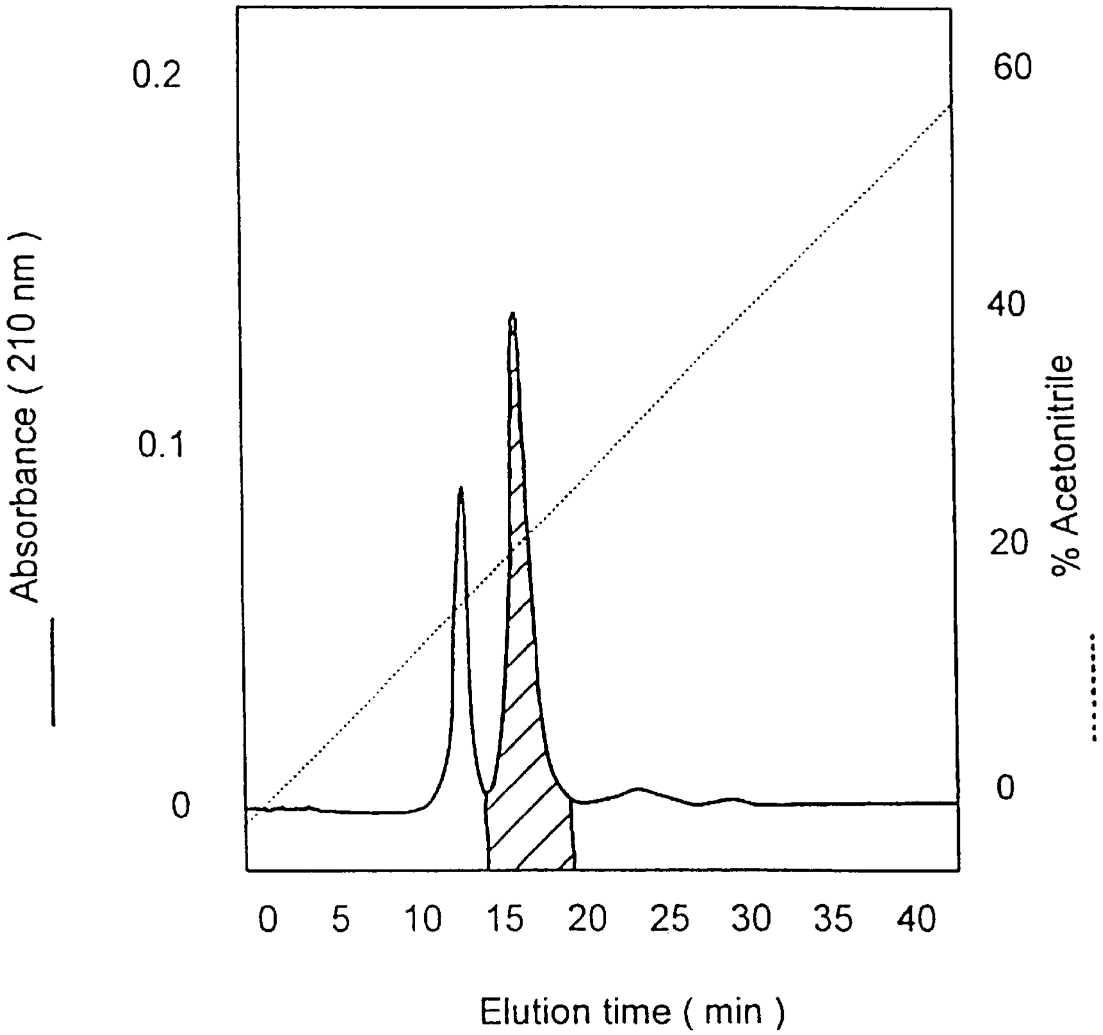
FIG. 5 shows the reversed phase chromatogram for purified Ib-AMP4.

An antimicrobial protein according to the invention is capable of being isolated from seeds of Aralia or Impatiens, and may also be capable of isolation from the seeds of both related and unrelated species, or may be produced or synthesised by any suitable method.

According to the present invention, there is further provided an antimicrobial protein having an amino acid sequence which is substantially homologous to a sequence selected from the group consisting of SEQ ID NO 10, SEQ ID NO 11, SEQ ID NO 12 and SEQ ID NO 13. A sequence is "substantially homologous" if it has at least 60% sequence identity with any one of the SEQ ID NOs 10 to 13 and it encodes a protein having antimicrobial activity.

The antimicrobial protein may be extracted and purified from plant material, manufactured from its known amino acid sequence by chemical synthesis using a standard peptide synthesiser, or produced within a suitable organism (for example, a micro-organism or plant) by expression of recombinant DNA. The antimicrobial protein is useful as a fungicide or an antibiotic and may be used for agricultural or pharmaceutical applications.

Amino acid sequencing of the Ib-AMPs is described in Examples 7 and 8. The amino acid sequence of Ib-AMP1 is shown as SEQ ID NO 10; the amino acid sequence of Ib-AMP2 is shown as SEQ ID NO 11; the amino acid sequence of Ib-AMP3 is shown as SEQ ID NO 12; the amino acid sequence of Ib-AMP4 is shown as SEQ ID NO 13. The four Ib-AMPs are very close homologues of each/other, but have no significant homology to the sequences of known proteins.

Knowledge of its primary structure enables manufacture of the antimicrobial protein, or parts thereof, by chemical synthesis using a standard peptide synthesiser. It also enables production of DNA constructs encoding the antimicrobial protein.

The invention further provides a DNA sequence encoding an antimicrobial protein according to the invention. The DNA sequence may be a cDNA sequence or a genomic sequence, and may be derived from a cDNA clone, a genomic DNA clone or DNA manufactured using a standard nucleic acid synthesiser.

The DNA sequence may be predicted from the known amino acid sequence and DNA encoding the protein may be manufactured using a standard nucleic acid synthesiser. Alternatively, the DNA sequence may be isolated from plant-derived DNA libraries. Suitable oligonucleotide probes may be derived from the known amino acid sequence and used to screen a cDNA library for cDNA clones encoding some or all of the protein. Cloning of the Ib-AMP cDNA is described in Example 8. Oligonucleotide probes or cDNA clones may be used to isolate the actual antimicrobial protein gene(s) by screening genomic DNA libraries. Such genomic clones may include control sequences operating in the plant genome. Thus it is also possible to isolate promoter sequences which may be used to drive expression of the antimicrobial (or other) proteins. These promoters may be particularly responsive to environmental conditions (such as the presence of a fungal pathogen), and may be used to drive expression of any target gene.

The DNA sequence encoding the antimicrobial protein may be incorporated into a DNA construct or vector in combination with suitable regulatory sequences (promoter, terminator, etc). The DNA sequence may be placed under the control of a constitutive or an inducible promoter (stimulated by, for example, environmental conditions, presence of a pathogen, presence of a chemical). Such a DNA construct may be cloned or transformed into a biological system which allows expression of the encoded protein or an active part of the protein. Suitable biological systems include micro-organisms (for example, bacteria such as *Escherichia coli*, Pseudomonas and endophytes such as *Clavibacter xyli* subsp. *cynodontis* (Cxc); yeast; viruses; bacteriophages; etc), cultured cells (such as insect cells, mammalian cells) and plants. In some cases, the expressed protein may subsequently be extracted and isolated for use.

An antimicrobial protein a ccording to the invention is useful as a fungicide or an antibiotic. The invention further provides a process of combating fungi or bacteria whereby they are exposed to an antimicrobial protein according to the invention.

For pharmaceutical applications, the antimicrobial protein may be used as a fungicide or anti-bacterial to treat mammalian infections (for example, to combat yeasts such as Candida).

An antimicrobial protei n ac cording to the invention may also be used as a preservative (for example, a s a food additive).

For agricultural applications, the antimicrobial protein may be used to improve the disease-resistance or disease-tolerance of crops either during the life of the plant or for post-harvest crop protection. Pathogens exposed to the proteins are inhibited. The antimicrobial protein may eradicate a pathogen already established on the plant or may protect the plant from future pathogen attack. The eradicant effect of the protein is particularly advantageous.

Exposure of a plant pathogen to an antimicrobial protein may be achieved in various ways, for example:

(a) a composition comprising the isolated protein may be applied to plant parts or the surrounding soil using standard agricultural techniques (such as spraying); the protein may have been extracted from plant tissue or chemically synthesised or extracted from micro-organisms genetically modified to express the protein;

(b) a composition comprising a micro-organism genetically modified to express the antimicrobial protein may be applied to a plant or the soil in which a plant grows;

(c) an endophyte genetically modified to express the antimicrobial protein may be introduced into the plant tissue (for example, via a seed treatment process);

[An endophyte is defined as a micro-organism having the ability to enter into non-pathogenic endosymbiotic relationships with a plant host. A method of endophyte-enhanced protection of plants has been described in a series of patent applications by Crop Genetics International Corporation (for example, International Application Publication Number WO90/13224, European Patent Publication Number EP-125468-B1, International Application Publication Number WO91/10363, International Application Publication Number WO87/03303). The endophyte may be genetically modified to produce agricultural chemicals. International Patent Application Publication Number WO94/16076 (ZENECA Limited) describes the use of endophytes which have been genetically modified to express a plant-derived antimicrobial protein].

(d) DNA encoding an antimicrobial protein may be introduced into the plant genome so that the protein is expressed within the plant body (the DNA may be cDNA, genomic DNA or DNA manufactured using a standard nucleic acid synthesiser).

Plant cells may be transformed with recombinant DNA constructs according to a variety of known methods (Agrobacterium Ti plasmids, electroporation, microinjection, microprojectile gun, etc). The transformed cells may then in suitable cases be regenerated into whole plants in which the new nuclear material is stably incorporated into the genome. Both transformed monocotyledonous and dicotyledonous plants may be obtained in this way, although the latter are usually more easy to regenerate. Some of the progeny of these primary transformants will inherit the recombinant DNA encoding the antimicrobial protein(s).

The invention further provides a plant having improved resistance to a fungal or bacterial pathogen and containing recombinant DNA which expresses an antimicrobial protein according to the invention. Such a plant may be used as a parent in standard plant breeding crosses to develop hybrids and lines having improved fungal or bacterial resistance.

Recombinant DNA is heterologous DNA which has been introduced into the plant or its ancestors by transformation. The recombinant DNA encodes an antimicrobial protein expressed for delivery to a site of pathogen attack (such as the leaves). The DNA may encode an active subunit of an antimicrobial protein.

A pathogen may be any fungus or bacterium growing on, in or near the plant. In this context, improved resistance is defined as enhanced tolerance to a fungal or bacterial pathogen when compared to a wild-type plant. Resistance may vary from a slight increase in tolerance to the effects of the pathogen (where the pathogen in partially inhibited) to total resistance so that the plant is unaffected by the presence of pathogen (where the pathogen is severely inhibited or killed). An increased level of resistance against a particular pathogen or resistance against a wider spectrum of pathogens may both constitute an improvement in resistance. Transgenic plants (or plants derived therefrom) showing improved resistance are selected following plant transformation or subsequent crossing.

Where the antimicrobial protein is expressed within a transgenic plant or its progeny, the fungus or bacterium is exposed to the protein at the site of pathogen attack on the plant. In particular, by use of appropriate gene regulatory sequences, the protein may be produced in vivo when and where it will be most effective. For example, the protein may be produced within parts of the plant where it is not normally expressed in quantity but where disease resistance is important (such as in the leaves).

Examples of genetically modified plants which may be produced include field crops, cereals, fruit and vegetables such as: canola, sunflower, tobacco, sugarbeet, cotton, soya, maize, wheat, barley, rice, sorghum, tomatoes, mangoes, peaches, apples, pears, strawberries, bananas, melons, potatoes, carrot, lettuce, cabbage, onion.

As the antimicrobial proteins of the invention are very active against some of the major maize pathogens, it would be particularly advantageous to transform maize plants with constructs encoding said proteins. Alternatively, the proteins may be supplied to maize plants by any other suitable method.

A further aspect of this invention relates generally to the expression of "polyproteins" in transgenic plants. A "polyprotein" is defined as two or more peptides linked together to form a single translation product. The component peptides are separated by cleavage sites whereby the expressed polyprotein is post-translationally processed into the component molecules. Such cleavage is achieved by the action of proteases or by self-processing of the polyprotein.

The relative levels of expression of several introduced genes in transgenic plants is notoriously influenced by "position effects" determined by the particular site of transgene integration into the genome. Even when introduced genes are linked on the same T-DNA, driven either by convergent or divergent promoters, they are usually not coordinately expressed at similar levels. This poses particular problems when high level expression of a number of introduced activities is required, for instance when attempting to express novel biochemical pathways in plants. In an attempt to achieve tissue specific, coordinated expression of two proteins, researchers have linked genes by co-transference on the same T-DNA but expression levels were found to vary independently. Another strategy was to link genes via adjacent and divergent promoters, but consistently coordinated expression was not obtained.

Linking proteins in the form of polyproteins is a strategy adopted in the replication of many viruses. On translation, virus-encoded proteinases mediate extremely rapid intramolecular (cis) cleavages of the polyprotein to yield discrete protein products. International Patent Application Number PCT/GB94/02765 (filed on Dec. 19, 1994) describes a method for the expression of multiple proteins in a transgenic plant comprising inserting into the genome of the plant a gene construct comprising a 5'-region which includes a promoter which is capable of initiating transcription of a structural gene under the control thereof, a protein encoding sequence coding for more than one protein and a 3'-terminator region which includes a polyadenylation signal, each of the said protein encoding sequences being separated from an adjacent protein encoding sequence by a DNA sequence which on translation provides a cleavage site whereby the expressed polyprotein is post-translationally processed into the component protein molecules. Preferably the DNA sequence which encodes the post-translation cleavage site is derived from a virus, particularly a picornavirus such as a Foot-and-Mouth Disease (FMD) virus. Thus multiple genes are inserted into a plant genome under the control of a single promoter, in the form of a self-processing polyprotein. The inclusion of proteinase or cleavage sequences in plant transformation constructs enables the expression from a single promoter of multiple introduced proteins, initially linked as a polyprotein, in plant cells and plants.

In work leading to the present invention, we have shown that the four Ib-AMP proteins are encoded by a single gene (SEQ ID NO 8, Example 8). The Ib-AMP gene sequence has an open reading frame of 333 amino acids (a polyprotein) containing six homologous repeats encoding all four of the isolated Ib-AMPs. The gene also contains seven propeptide domains which are removed during processing of the precursor protein: five of these domains (SEQ ID NO 14 to SEQ ID NO 18) are spacers which lie between the AMP-encoding regions; one of the domains (SEQ ID NO 20) lies at the C-terminus of the protein; one of the domains (SEQ ID NO 19) lies at the N-terminus of the protein and is linked to a signal sequence (SEQ ID NO 21) of approximately 25 amino acids. The structure of the Ib-AMP gene is shown in FIG. 10 and described in Example 8. In plants only two examples are known of multidomain precursors which are cleaved into near identical parts, namely polyubiquitin (Christensen et al, Plant Mol Biol, 18:675–689) and a proteinase inhibitor from *Nicotiana alata* (Atkinson et al, Plant Cell, 5:203–213).

According to a further aspect of the invention, there is provided a method for the expression of multiple proteins in a transgenic plant comprising inserting into the genome of the plant a gene construct comprising a 5'-region which includes a promoter which is capable of initiating transcription of a structural gene under the control thereof, at least two protein encoding sequences and a 3'-terminator region which includes a polyadenylation signal, each of the said protein encoding sequences being separated from an adjacent protein encoding sequence by a DNA sequence which on translation provides a cleavage site whereby the expressed polyprotein is post-translationally processed into the component protein molecules, wherein at least one of the DNA sequences providing the cleavage site encodes an amino acid sequence selected from the group consisting of SEQ ID NO 14, SEQ ID NO 15, SEQ ID NO 16, SEQ ID NO 17 and SEQ ID NO 18. It is well known that variations may be made in amino acid sequences which do not greatly affect function and it is intended that such variants of the said sequence and the nucleotide which encodes it are within the scope of this invention. The DNA sequences providing the cleavage site may be derived from SEQ ID NO 8.

Insertion of any one of the five Ib-AMP spacer propeptide domains (SEQ ID NO 14 to SEQ ID NO 18) to link protein encoding sequences allows the engineering of plant expression vectors where multiple whole proteins or protein domains can be expressed as a polyprotein and cleaved apart co-translationally with high efficiency. Use of the plant-derived spacer sequences facilitates processing of the polyprotein within transgenic plant tissue. The other propeptide domains (SEQ ID NO 19, SEQ ID NO 20) and the signal peptide (SEQ ID NO 21) from the Ib-AMP gene may also be incorporated into the plant expression vector.

Thus the Ib-AMP gene arrangement may be used in the expression of other peptides or proteins (including other antimicrobial peptides) by using the conserved spacer propeptide domains to construct an artificial gene encoding multimers of a given protein. The protein components of the polyprotein may be identical, thus increasing expression of said protein through a type of "gene-dosage" effect. Alternatively, two or more different protein components may be linked in one polyprotein, enabling coordinated expression of the different proteins. For example, this may enable the rapid introduction of entire enzyme cascades into plants.

The invention is also described with reference to the SEQUENCE LISTING in which:

SEQ ID NO 1 is the partial amino acid sequence of Ib-AMP1 shown in FIG. 9;

SEQ ID NO 2 is the partial amino acid sequence of Ib-AMP2 shown in FIG. 9;

SEQ ID NO 3 is the partial amino acid sequence of Ib-AMP3 shown in FIG. 9;

SEQ ID NO 4 is the partial amino acid sequence of Ib-AMP4 shown in FIG. 9;

SEQ ID NO 5 is the amino acid sequence of a region of the Ib-AMP sequences;

SEQ ID NO 6 is the nucleotide sequence of the oligonucleotide IbAMP1-C;

SEQ ID NO 7 is the nucleotide sequence of the oligonucleotide IbAMP1-B;

SEQ ID NO 8 is the nucleotide sequence of the Ib-AMP cDNA as shown in FIG. 10;

SEQ ID NO 9 is the predicted amino acid sequence of the protein encoded by the Ib-AMP cDNA as shown in FIG. 10;

SEQ ID NO 10 is the complete amino acid sequence of Ib-AMP1;

SEQ ID NO 11 is the complete amino acid sequence of Ib-AMP2;

SEQ ID NO 12 is the complete amino acid sequence of Ib-AMP3;

SEQ ID NO 13 is the complete amino acid sequence of Ib-AMP4.

SEQ ID NO 14 is the amino acid sequence of an Ib-AMP propeptide spacer domain;

SEQ ID NO 15 is the amino acid sequence of an Ib-AMP propeptide spacer domain;

SEQ ID NO 16 is the amino acid sequence of an Ib-AMP propeptide spacer domain;

SEQ ID NO 17 is the amino acid sequence of an Ib-AMP propeptide spacer domain;

SEQ ID NO 18 is the amino acid sequence of an Ib-AMP propeptide spacer domain;

SEQ ID NO 19 is the amino acid sequence of the Ib-AMP N-terminal propeptide spacer domain;

SEQ ID NO 20 is the amino acid sequence of the Ib-AMP C-terminal propeptide spacer domain;

SEQ ID NO 21 is the amino acid sequence of the Ib-AMP signal peptide.

EXAMPLE 1

Antifungal and Antibacterial Activity Assays

Antifungal activity was measured by microspectrophotometry as previously described (Broekaert, 1990, FEMS Microbiol Lett, 69:55–60). Routinely, tests were performed with 20 μl of a (filter-sterilized) test solution and 80 μl of a suspension of fungal spores ($2\times10^4$ spores/ml) in Medium A (half strength potato dextrose broth or ½ PDB) or Medium B (½ PDB supplemented with 1 mM $CaCl_2$ and 50 mM KCl). Control microcultures contained 20 μl of sterile distilled water and 80 μl of the fungal spore suspension.

Unless otherwise stated the test organism was *Fusarium culmorum* (strain IMI 180420) and incubation was done at 25° C. for 48 hours. Percent growth inhibition is defined as 100 times the ratio of the corrected absorbance of the control microculture minus the corrected absorbance of the test microculture over the corrected absorbance at 595 nm of the control microculture. The corrected absorbance values equal the absorbance at 595 nm of the culture measured after 48 hours minus the absorbance at 595 nm measured after 30 min.

Antibacterial activity was measured microspectrophotometrically as follows. A bacterial suspension was prepared by inoculating soft nutrient agarose (tryptone, 10 g/l; Seaplaque agarose (FMC), 5 g/l). Aliquots (80 μl) of the bacterial suspension ($10^5$ colony forming units per ml) were added to filter-sterilized samples (20 μl) in flat-bottom 96-well microplates. The absorbance at 595 nm of the culture was measured with the aid of a microplate reader after 30 minutes and 24 hours of incubation at 28° C. Percent growth inhibition was calculated as described above for the antifungal activity assay.

EXAMPLE 2

Purification of Antimicrobial Proteins from *Impatiens balsamina* Seeds

Five hundred grammes of *I balsamina* seeds (purchased from Chiltern Seeds, Cumbria, UK) was ground in a coffee mill and the resulting meal was extracted for 2 hours at 4° C. with 2 litres of an ice-cold extraction buffer containing 10 mM $NaH_2PO_4$, 15 mM $Na_2HPO_4$, 100 mM KCl, 2 mM EDTA and 1 mM benzamidine. The resulting homogenate was squeezed through cheesecloth and clarified by centrifugation (30 min at 7,000×g). Solid ammonium sulphate was added to the supernatant to obtain 75% relative saturation and the precipitate allowed to form by standing overnight at 4° C. Following centrifugation at 7,000 ×g for 30 minutes, the precipitate was redissolved in a minimal volume of distilled water and dialyzed extensively against distilled water using benzoylated cellulose tubing (Sigma, St Louis, Mo.). After dialysis the solution was adjusted to 50 mM $(NH_4)Ac$ (pH 9) by addition of the ten-fold concentrated buffer, and subsequently passed over a Q-Sepharose Fast Flow (Pharmacia, Uppsala, Sweden) column (12×5 cm) in equilibrium with 50 mM $NH_4Ac$ (pH 9). The basic protein fraction which passed through the column was adjusted to pH6 with acetic acid and further purified by cation exchange chromatography as described below.

Approximately 500 ml of the basic protein fraction was applied on a S-Sepharose High Performance (Pharmacia) column (10×1.6 cm) previously equilibrated with 50 mM $NH_4Ac$ buffer (pH 6.0). The column was eluted at 3 ml\min with a linear gradient of 50–750 mM $NH_4Ac$ (pH 6) over 325 minutes. The eluate was monitored for protein by online measurement of the absorbance at 280 nm and collected in 10 ml fractions. Samples from each fraction were assayed for antifungal activity as described in Example 1. Results are shown in FIG. 1, with the active peaks shaded black.

Following chromatography, the extract yielded four peaks of activity eluting at between 400 mM and 700 mM $NH_4Ac$. Fractions from each peak showing antifungal activity were pooled and further purified by reverse-phase HPLC. About 3 mg amounts of each peak were loaded on a Pep-S (porous silica $c_2/C_{18}$, Pharmacia) column (25×0.93 cm) equilibrated with 0.1% TFA (trifluoracetic acid). The column was developed at 1 ml/min with a linear gradient of 0.1% TFA to 100% acetonitrile/0.1% TFA over 65 minutes. The eluate was monitored for protein by online measurement of the absorption at 210 nm.

The results for peaks 1, 2, 3 and 4 are shown in FIGS. 2, 3, 4 and 5, respectively. One ml fractions were collected, vacuum dried, and finally dissolved in 0.5 ml distilled water. 10 $\mu$l from each fraction was assayed for antifungal activity. Peaks 1, 2 and 3 yielded single peaks of antifungal activity (shaded black) which eluted at approximately 20% acetonitrile. The active fractions in peaks 1, 2 and 3 are designated Ib-AMP1, Ib-AMP2 and Ib-AMP3 respectively. Peak 4 yielded two peaks of antifungal activity, the second larger peak is designated Ib-AMP4 (shaded black in FIG. 5). The first peak probably represents some carry over from peak 3 on the FPLC.

EXAMPLE 3

Purification of Antimicrobial Proteins from *Aralia chinensis* Seeds.

The basic protein fraction was extracted from *A chinensis* seeds (purchased from Sandeman Seeds, Pulborough, Sussex, UK) using the method described in Example 2. This protein fraction was then further purified using the method described in Example 2.

Figure 6:
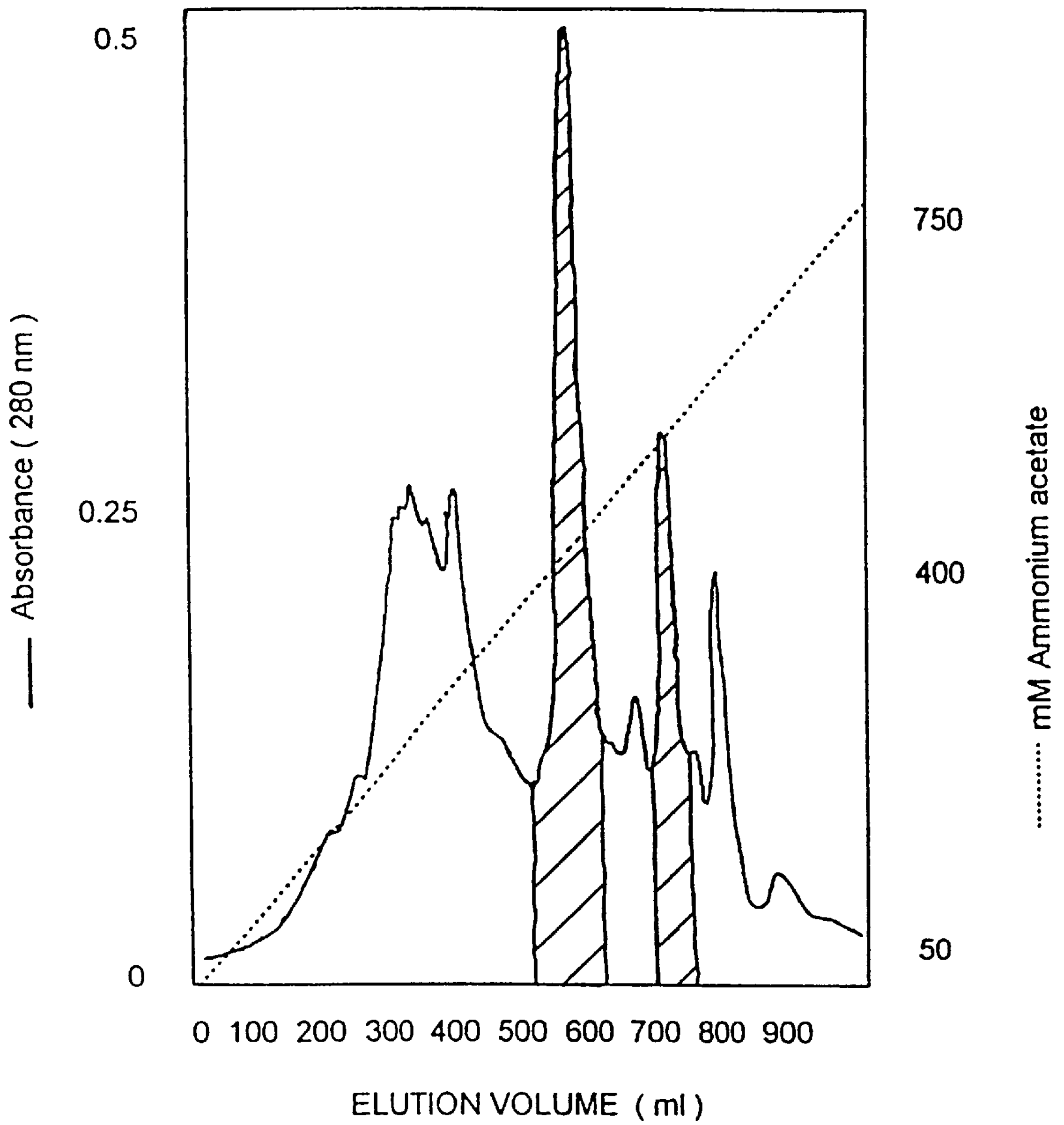
FIG. 6 shows the cation exchange chromatogram for purification of the Arc-AMPs.

Following chromatography on the S-Sepharose High Performance column, the Aralia extract yielded two peaks of antifungal activity eluting at approximately 400 mM (peak 1) and 500 mM (peak 2) $NH_4Ac$. Results are shown in FIG. 6, with the two active peaks shaded in black.

Figure 7:
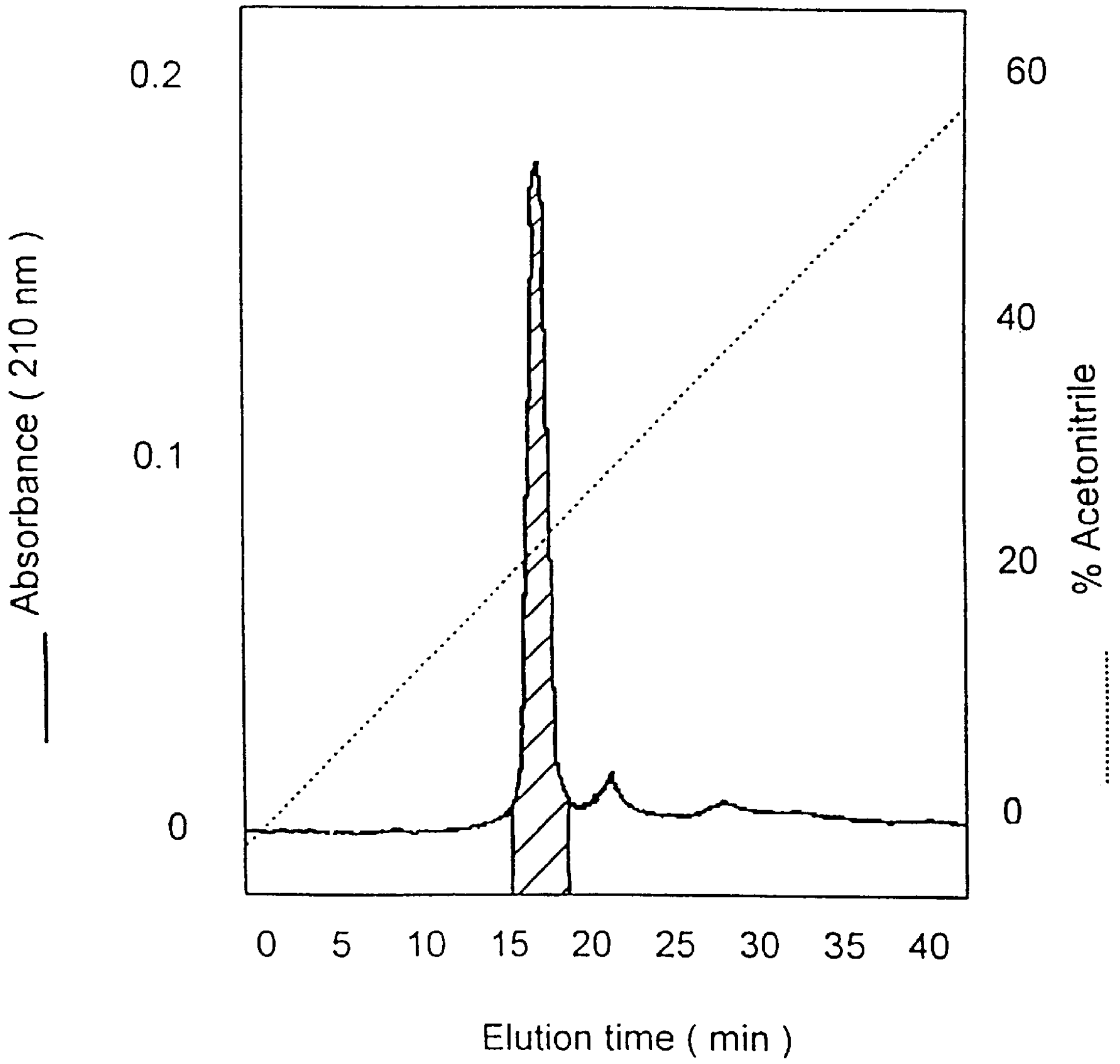
FIG. 7 shows the reversed phase chromatogram for purified Arc-AMP1.
Figure 8:
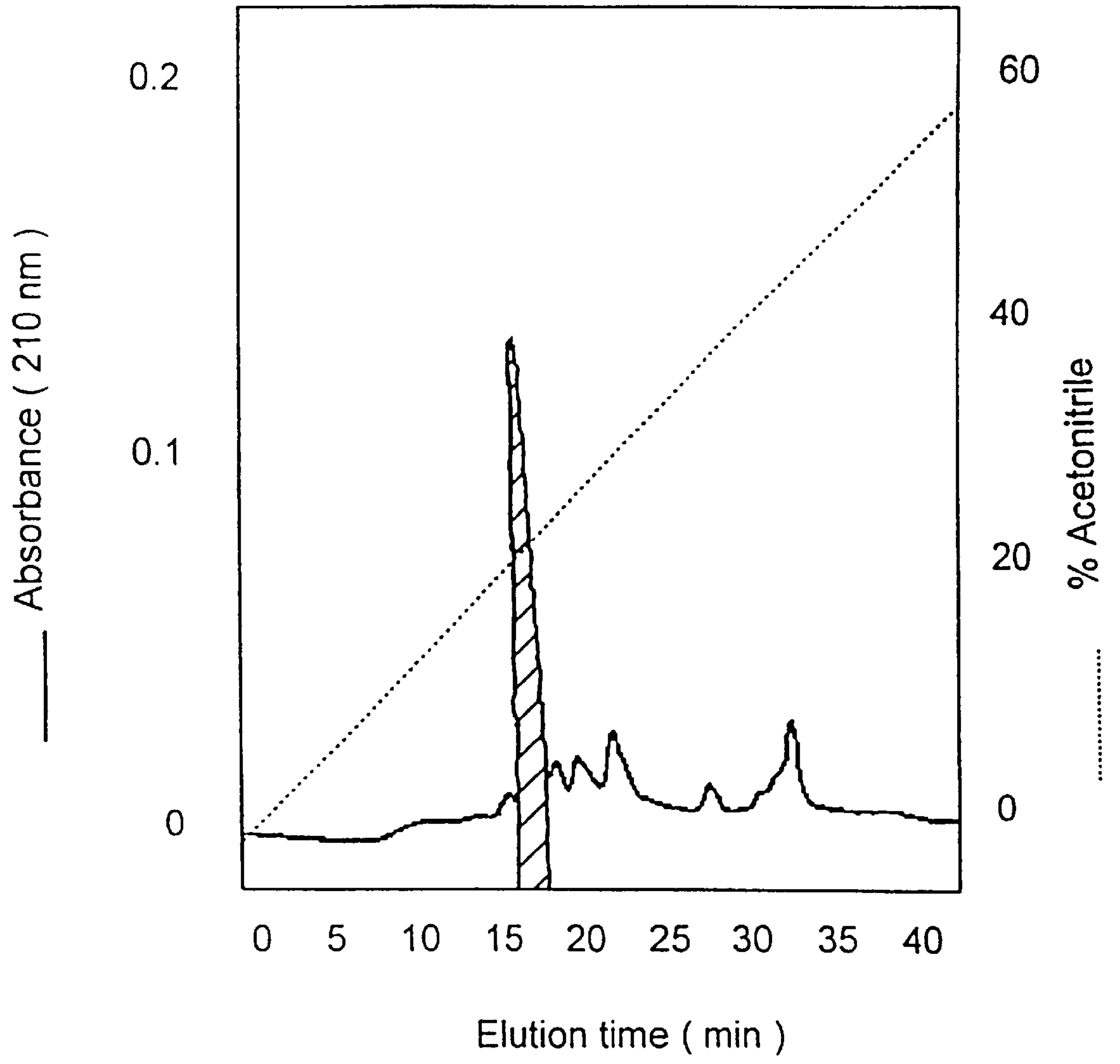
FIG. 8 shows the reversed phase chromatogram for purified Arc-AMP2.

Active fractions were pooled for each peak and further purified on reverse-phase HPLC as described in Example 2. Results for peak 1 are shown in FIG. 7: it yielded an active factor eluting at approximately 20% acetonitrile which is designated Arc-AMP1. Similarly peak 2 eluted to a single peak of activity which is designated Arc-AMP2 (results shown in FIG. 8).

EXAMPLE 4

Molecular Structure of the Purified Antimicrobial Proteins

The molecular structure of the purified antimicrobial proteins was further analysed by sodium dodecyl sulphate polyacrylamide gel electrophoresis (SDS-PAGE). SDS-PAGE was performed on precast commercial gels (PhastGel High Density from Pharmacia) using a PhastSystem (Pharmacia) electrophoresis apparatus. The sample buffer contained 200 mM Tris-HCl (pH 8.3), 1% (w/v) SDS, 1 mM EDTA, 0.005% bromophenol blue and, unless otherwise stated, 1% (w/v) dithioerythritol (DTE). Proteins were visualised after diffusion blotting to nitrocellulose followed by silver staining. Molecular weight markers (Pharmacia) and purified Mj-AMP2 (4 kDa protein from *Mirabilis Jalapa* seeds) were run for comparison.

Ib-AMP1 and Arc-AMP1 were analysed by SDS-PAGE. Both proteins run as approximately 3 kDa bands when run reduced and also when run non-reduced. The results show that the peptides are single chain polypeptides.

EXAMPLE 5

Antifungal Potency of the Antimicrobial Proteins

The antifungal potency of the purified proteins was assessed on different plant pathogenic fungi, using the assay described in Example 1. Growth of fungi, collection and harvest of fungal spores were done as previously described (Broekaert et al, 1990, FEMS Microbiol Lett, 69:55–60). The following fungal strains were used: *Alternaria longipes* CBS62083, *Bipolaris maydis* HM-10, *Botrytis cinerea* MUCL 30158, *Cercospora beticola* strain K897, *Colletotrichum graminicola* CG-17, *Cladosporium sphaerospermum KO*791, *Fusarium culmorum* IMI 180420, *Fusarium graminearum* FR-12, *Fusarium moniliforme* FM-9, *Penicillium digitatum* (K0879), *Sphacelotheca reiliana* HS, *Septoria tritici* (K1097D), *Stenocarpella maydis*, *Trichoderma viride* K1127, *Verticillium albo-atrum* K0937, *Verticillium dahliae* MUCL 19210.

Serial dilutions of the antifungal proteins were applied to the fungi, either using growth medium A (half strength potato dextrose broth, ½ PDB) or medium B (medium A supplemented with 1 mM $CaCl_2$ and 50 mM KCl). The percent growth inhibition was measured by microspectrophotometry. The concentration required for 50; growth inhibition after 48 h of incubation ($IC_{50}$ value) was calculated from the dose-reponse curves.

The results for Ib-AMP1, Ib-AMP2, Ib-AMP3 and Ib-AMP4 are summarised in Table 1. The results for Arc-AMP1 and Arc-AMP2 are summarised in Table 2. All six peptides show broad spectrum activity against the pathogens tested. In the low-ionic strength medium (medium A) the $IC_{50}$ values are generally below 10 $\mu$g/ml. The activity of the peptides is sensitive to the ionic conditions used in the assay and in high salt medium (medium B) their activity is reduced. However, even in medium B. the most basic of the Ib-AMP peptides (Ib-AMP4) still exhibits fairly strong activity on some of the fungi tested.

TABLE 1

ANTIFUNGAL ACTIVITY OF THE Ib-AMPs

| | IC50 ($\mu$g/ml) | | | |
|---|---|---|---|---|
| FUNGUS | Ib-AMP1 | Ib-AMP2 | Ib-AMP3 | Ib-AMP4 |
| MEDIUM A | | | | |
| *A longipes* | 3 | 12 | 6 | 3 |
| *B cinerea* | 12 | 25 | 6 | 6 |
| *B maydis* | 7 | nd | nd | nd |
| *C beticola* | 1.5 | 3 | nd | nd |
| *C graminicola* | 2 | nd | nd | nd |
| *C sphaerospermum* | 1.5 | 6 | 3 | 1 |
| *F culmorum* | 1.5 | 6 | 6 | 1 |
| *F graminearum* | 3 | nd | nd | nd |
| *F moniliforme* | 20 | nd | nd | nd |
| *P digitatum* | 3 | 6 | 3 | 3 |
| *S maydis* | 5 | nd | nd | nd |
| *S reiliana* | 4 | nd | nd | nd |

TABLE 1-continued

ANTIFUNGAL ACTIVITY OF THE Ib-AMPs

| FUNGUS | IC50 (μg/ml) Ib-AMP1 | Ib-AMP2 | Ib-AMP3 | Ib-AMP4 |
|---|---|---|---|---|
| *S tritici* | 1 | nd | nd | 1 |
| *T viride* | 6 | 12 | 12 | 6 |
| *V albo-atrum* | 3 | 12 | 6 | 6 |
| *V dahliae* | 1 | nd | nd | nd |
| MEDIUM B | | | | |
| *A longipes* | 50 | >200 | >200 | 12 |
| *B cinerea* | >200 | >200 | >200 | 200 |
| *C sphaerospermum* | 50 | >200 | 100 | 6 |
| *F culmorum* | 50 | >200 | 100 | 6 |
| *P digitatum* | 200 | >200 | 100 | 25 |
| *S tritici* | 50 | nd | nd | 12 |
| *T viride* | >200 | >200 | >200 | 150 |
| *V albo-atrum* | >200 | >200 | >200 | 50 |

nd — not determined

TABLE 2

ANTIFUNGAL ACTIVITY of Arc-AMP1 and Arc-AMP2

| | IC50 (μg/ml) | | | |
|---|---|---|---|---|
| | Medium A | | Medium B | |
| Fungus | ArcAMP1 | ArcAMP2 | ArcAMP1 | ArcAMP2 |
| *B cinerea* | 10 | 8 | >100 | >100 |
| *C sphaerospermum* | 1.5 | 1 | 100 | 100 |
| *F culmorum* | 1 | 1 | 100 | 100 |
| *P digitatum* | 2 | 3 | >100 | >100 |
| *V dahliae* | 1 | nd | 50 | nd |

nd = not determined

EXAMPLE 6

Anti-bacterial and Anti-yeast Activity of Ib-AMP1 and Arc-AMP1

The purified proteins were assessed for their effect on the growth of the following bacteria: *Bacillus megaterium* ATCC 13632 and *Escherichia coli* strain HB101. The proteins were also assessed for their effect on the growth of *Saccharomyces cerevisiae* JRY188 and *Candida albicans* KA-1. Bioassays were carried out as described in Example 1. The results are summarised in Table 3. Both proteins strongly inhibited the growth of *B megaterium* and *S cerevisiae* but had little or no effect on the growth of *E coli.* Ib-AMP1 also strongly inhibited the growth of *C albicans.*

TABLE 3

Activity on bacteria and yeast

| Fungus | IC50 (μg/ml) Ib-AMP1 | Arc-AMP1 |
|---|---|---|
| *B megaterium* | 10 | 15 |
| *E coli* | >800 | >500 |
| *S cerevisiae* | 20 | 30 |
| *C albicans* | 10 | nd |

nd — not determined

EXAMPLE 7

Amino Acid Sequencing of Ib-AMPs

Cysteine residues were modified by S-pyridylethylation using the method of Fullmer (1984, Anal Biochem, 142, 336–341). Reagents were removed by HPLC on a Pep-S (porous silica $C_2/C_{18}$) (Pharmacia) column (25×0.4 cm). The s-pyridylethylated proteins were recovered by eluting t he colum n with a linear gradient from 0.1; trifluoroacetic acid (TFA) to acetonitrile containing 0.1% TFA. The resulting protein fractions were subjected to amino acid sequence analysis in a 477A Protein Sequence (Applied Biosystems) with on-line detection of phenylthiohydantoin amino acid derivatives in a 120A Analyser (Applied Biosystems).

Initial attempts to sequence the Ib-AMPs showed that all four peptides were N-terminally blocked. In order to obtain their sequence, each of the peptides was digested with either trypsin or chymotrypsin. The resulting peptide fragments were purified by RP-HPLC and sequenced. In each case one peptide fragment (the N-terminus of the protein) was found to be blocked, preventing complete sequencing of the Ib-AMP proteins.

Digestion of Ib-AMP1 with trypsin gave four fragments from which the partial sequence of Ib-AMP1 (SEQ ID NO 1) was obtained. Fragment Ib1T1 was 16 amino acid long and contained the majority of Ib-AMP1 (as shown in FIG. 9). The other three peptide fragments represented further cleavage of peptide Ib1T1. In addition, sequencing of a peptide (Ib1C1) generated by digestion of Ib-AMP1 with chymotrypsin allowed two further amino acids to be assigned to the N-terminus.

The partial sequences for Ib-AMP2 (SEQ ID NO 2), Ib-AMP3 (SEQ ID NO 3) and Ib-AMP4 (SEQ ID NO 4) were assembled in a similar way from sequences of peptide fragments generated by chymotrypsin digestion (FIG. 9). Only two fragments from Ib-AMP3 were sequenced and so the sequence shown in FIG. 9 (SEQ ID NO 3) represents only the 11 amino acids from the C-terminus of this peptide.

In order to estimate the full-length of the Ib-AMPs, the molecular weight of Ib-AMP1 was determined by electrospray mass spectrometry and found to be 2466 Da. The molecular weight of the 18 amino acids assigned by amino acid sequencing is 2172 Da suggesting that the full-length peptide is only 2 or 3 amino acids longer.

All the four Ib-AMP peptides are very close homologues of each other with only a few amino acid substitutions between them. Searches of protein databases have failed to find any other proteins with significant homology to the Ib-AMP sequences. However, a small part of the Ib-AMP sequences, the region GPGRRY (SEQ ID NO 5), has been found in a number of proteins (including viral coat proteins) and has been shown to be involved in forming a β-turn.

EXAMPLE 8

Molecular Cloning of the Impatiens cDNA

Total RNA was extracted from dry *Impatiens balsamina* seeds using the method of Jepson et al (1991, Plant Mol Biol Reporter, 9(2)). From 30 g seed, 5.9 mg of total RNA was recovered. Approximately 3 mg of total RNA was used to purify Poly (A)+ mRNA using the PolyAtrack Kit (Stratagene). This yielded approximately 30 μg of mRNA of which half was used for cDNA synthesis using Stratagene's lambda ZAPII phage vector kit according to the manufacturers instructions. Synthesised cDNA was size fractionated into 3 fractions; up to 6 Kb, up to 4 Kb and up to 2 Kb.

A DNA probe for screening the library was produced by polymerase chain reaction (PCR) using the synthesised cDNA fractions as template and two degenerate oligos based on the available peptide sequence for Ib-AMP1. The sequences of the PCR primers were:

IbAMP1-C (5'-GITGT/CTGT/CCGITGGGGICC-3') (SEQ ID NO 6) and

IbAMP1-B (5'-CACCAICT/GIACG/ACAG/ATA-3') (SEQ ID NO 7).

A PCR product of 50 bp was purified by polyacrylamide gel electrophoresis, random labelled and used to probe the library. Approximately 160,000 plaques were probed and 15 positives were obtained from this primary round of screening. These 15 plaques were purified by two further rounds of screening using the same DNA probe. Inserts from the purified plaques were excised in vivo into the pBluescript phagemid with the aid of a helper phage (VCSM13). Inserts were removed by digestion with Xho1 and EcoR1 and their sizes compared on agarose gels. The sizes of the inserts varied from approximately 600 bp to 1300 bp. Fourteen clones were subjected to nucleotide sequencing. Clone Ib22 was fully sequenced and shown to contain a complete gene sequence with an open reading frame of 333 amino acids containing six homologous repeats encoding all four of the isolated Ib-AMPs. Other clones were found to be either identical to clone Ib22 or truncated versions of the full-length gene.

FIG. 10 shows the nucleotide sequence (SEQ ID NO 8) of the Ib-AMP cDNA (clone Ib22) and the predicted amino acid sequence (SEQ ID NO 9) of the encoded protein which contains the repeated sequences (underlined in FIG. 10). By comparing this predicted sequence to the Ib-AMP sequences determined by direct peptide sequencing, the complete Ib-AMP sequences were identified. It was found that the first repeat encodes Ib-AMP3 (SEQ ID NO 12); the second, third and fourth repeats each encode Ib-AMP1 (SEQ ID NO 10); the fifth repeat encodes Ib-AMP2 (SEQ ID NO 11); and the sixth repeat encodes Ib-AMP4 (SEQ ID NO 13).

Thus the Ib-AMP gene contains three repeats of Ib-AMP1 and one each of Ib-AMP2, Ib-AMP3 and Ib-AMP4. The gene also contains a predicted signal sequence of approximately 25 amino acids and seven propeptide domains which are removed during processing of the precursor protein. Thus the structure of the polyprotein encoded by the Ib-AMP gene (FIG. 10) is as follows:

N-terminus—signal peptide (SEQ ID NO 21)—
—propeptide domain (SEQ ID NO 19)—
—Ib-AMP3 encoding region (SEQ ID NO 12)—
—propeptide domain (SEQ ID NO 14)—
—Ib-AMP1 encoding region (SEQ ID NO 10)—
—propeptide domain (SEQ ID NO 15)—
—Ib-AMP1 encoding region (SEQ ID NO 10)—
—propeptide domain (SEQ ID NO 16)—
—Ib-AMP1 encoding region (SEQ ID NO 10)—
—propeptide domain (SEQ ID NO 17)—
—Ib-AMP2 encoding region (SEQ ID NO 11)—
—propeptide domain (SEQ ID NO 18)—
—Ib-AMP4 encoding region (SEQ ID NO 13)—
—propeptide domain (SEQ ID NO 20)—C-terminus.

Five of the propeptide domains (SEQ ID NO 14 to SEQ ID NO 18) are "spacers" separating two Ib-AMP encoding regions. These spacers are cleaved at either end during post-translational processing of the polyprotein. The N-terminal propeptide domain (SEQ ID NO 19) is cleaved from the signal peptide (SEQ ID NO 21) at one end and from the Ib-AMP3 encoding region at the other end. The C-terminal propeptide region (SEQ ID NO 20) is cleaved from the Ib-AMP4 encoding region at one end.

EXAMPLE 9

Construction of the Plant Expression Vector pIB6 Containing the Ib-AMP cDNA

Figure 11:
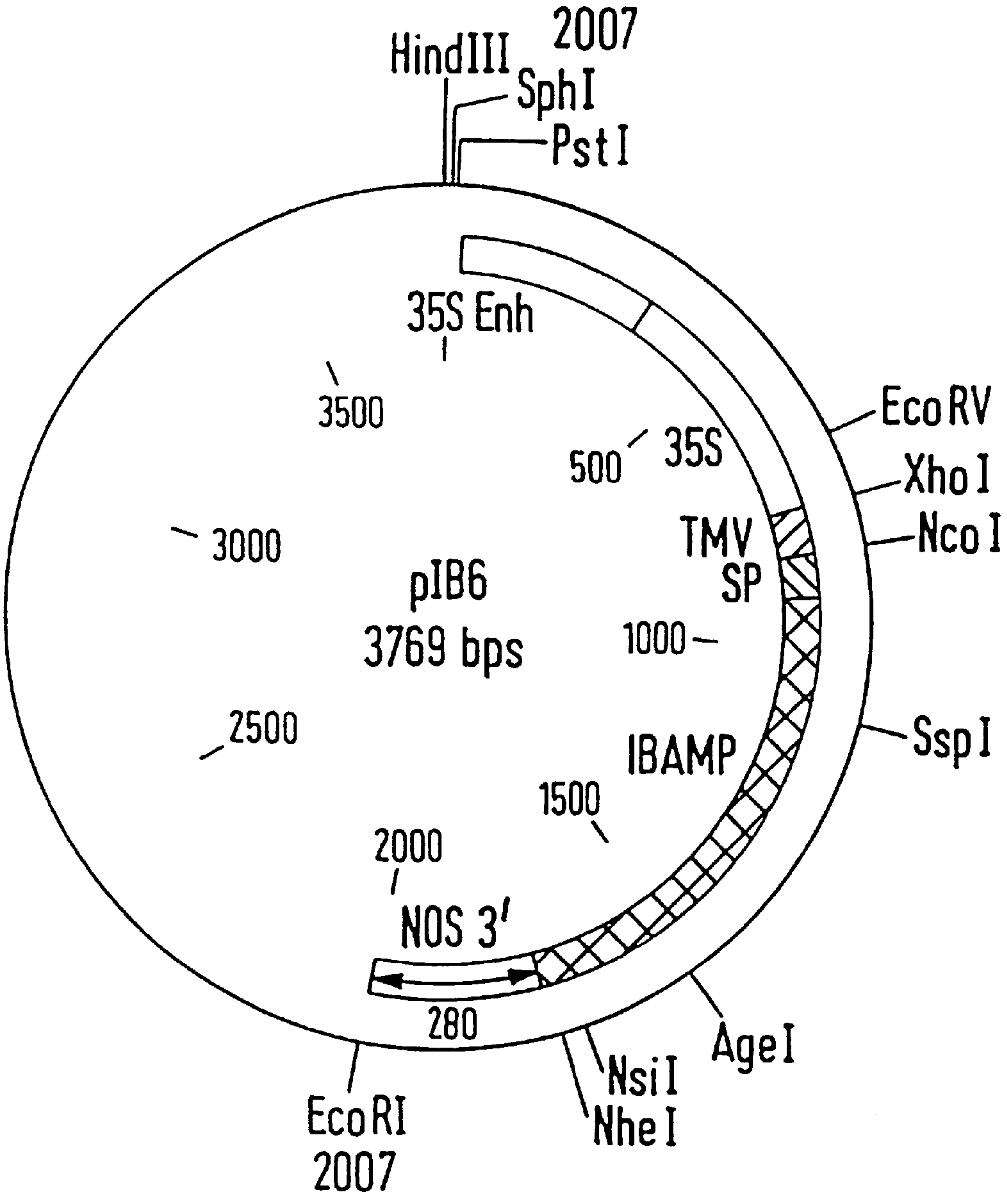
FIG. 11 is a diagram showing the structure of the vector pIB6.

The plant expression vector pIB6 was constructed using the pUC based vector pMJB1 which carries an enhanced 35S promoter, TMV leader sequence and the Nos terminator. An NcoI site was introduced using PCR at the start of the open reading frame in the Ib-AMP cDNA and the Ib-AMP cDNA subsequently cloned into pMJB1 at the NcoI and SmaI sites to create pIB6 (FIG. 11).

EXAMPLE 10

Construction of Plant Transformation Vector pBinIB6

Figure 12:
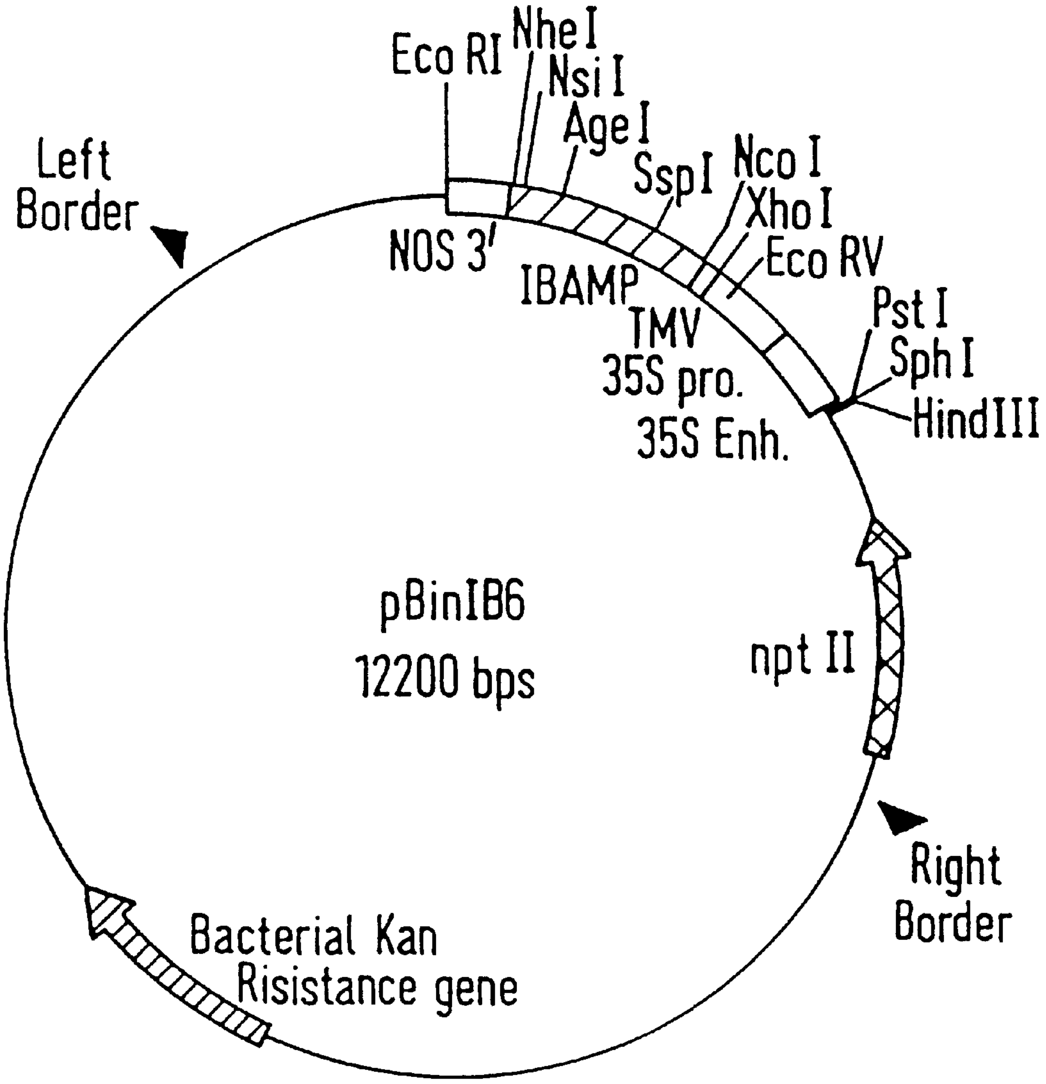
FIG. 12 is a diagram showing the structure of the vector pBinIB6.

The expression vector pIB6 was digested with HindIII and EcoR1 and the fragment containing the Ib-AMP expresssion cassette was subcloned into pBin19Ri. pBin19Ri is a modified version of the plant transformation vector pBin19 (Bevan 1984, Nucleic Acids Research 12, 8711–8721) wherein the unique EcoR1 and HindIII sites are switched and the defective nptII expression cassette (Yenofsky et al, 1990, Proc. Natl. Acad. Sci. USA 87, 3435–3439) is introduced. The new plant transformation vector is designated pBinIB6 (FIG. 12).

EXAMPLE 11

Plant Transformation

The disarmed *Acrobacterium tumefaciens* strain LBA4404 (pAL4404) (Hoekema et al, 1983, Nature 303, 179–180) was transformed with the vector pBinIB6 using the method of de Framond et al (Biotechnology 1, 262–269). Tobacco transformation was carried out using leaf discs of *Nicotiana tabacum* Samsun and co-culturing with Agrobacterium containing pBinIB6. A selection pressure of 100 μg/ml kanamycin was present during the co-cultivation. Transgenic plants transformed with pBinIB6 were regenerated on media containing 100 μg/ml kanamycin.

Transgenic plants are analysed for expression of the introduced gene using standard western blotting techniques and plants capable of constitutive expression are selected and self-pollinated to give seed. F1 seedlings of transgenic plants are further analysed and progressed to select plants homozygous for the Ib-AMP gene.

EXAMPLE 12

Making a DNA Construct Encoding a Polyprotein

An artificial gene is constructed using the DNA sequence encoding the antimicrobial protein Rs-AFP2 (International Patent Application Publication Number WO93/05153). The artificial gene comprises three copies of the Rs-AFP2 encoding sequence linked by two spacer regions, each spacer region encoding a propeptide linker having the sequence of any one of SEQ ID NO 14 to SEQ ID NO 18.

The artificial gene is constructed from the Rs-AFP2 sequence by introducing a suitable restriction enzyme site at the 3' end of the mature protein sequence, into which oligonucleotides encoding the linker peptide and further copies of the DNA encoding the 51 amino acid Rs-AFP2 peptide sequence are introduced. Each subsequent copy of the Rs-AFP2 peptide sequence is linked to the previous one using the linker peptide sequence. The final copy of the Rs-AFP2 encoding sequence is followed by a stop codon. The first copy of the Rs-AFP2 encoding sequence may be preceded by a signal sequence.

The artificial gene is then used to construct a plant expression construct suitable for plant transformation. A plant-operative promoter drives expression of the artificial gene so that the polyprotein is produced and subsequently processed to release three copies of the Rs-AFP2 protein.

What is claimed is:

1. A recombinant DNA encoding an antimicrobial protein having an amino acid sequence selected from the group consisting of SEQ ID NO: 10, SEQ ID NO: 11, SEQ ID NO: 12 and SEQ ID NO: 13.

2. The recombinant DNA as claimed in claim 1 comprising a nucleotide sequence selected from the group consisting of bases 181 to 240 of SEQ ID NO: 8, bases 325 to 384 of SEQ ID NO: 8, bases 463 to 522 of SEQ ID NO: 8, bases 607 to 666 of SEQ ID NO: 8, bases 715 to 774 of SEQ ID NO: 8 and bases 853 to 921 of SEQ ID NO: 8.

3. A biological system comprising DNA as claimed in claim 1.

4. The biological system as claimed in claim 3 which is a micro-organism.

5. The biological system as claimed in claim 3 which is a plant.

6. A transgenic plant comprising the recombinant DNA as claimed in claim 1.

* * * * *

```
                              SEQUENCE LISTING


(1) GENERAL INFORMATION:

   (iii) NUMBER OF SEQUENCES: 21


(2) INFORMATION FOR SEQ ID NO: 1:

     (i) SEQUENCE CHARACTERISTICS:
          (A) LENGTH: 18 amino acids
          (B) TYPE: amino acid
          (C) STRANDEDNESS: single
          (D) TOPOLOGY: linear

    (ii) MOLECULE TYPE: peptide

    (vi) ORIGINAL SOURCE:
          (A) ORGANISM: FIGURE 9, IB-AMP1

    (xi) SEQUENCE DESCRIPTION: SEQ ID NO: 1:

Gly Arg Arg Cys Cys Gly Trp Gly Pro Gly Arg Arg Tyr Cys Val Arg
1               5                   10                  15

Trp Cys


(2) INFORMATION FOR SEQ ID NO: 2:

     (i) SEQUENCE CHARACTERISTICS:
          (A) LENGTH: 18 amino acids
          (B) TYPE: amino acid
          (C) STRANDEDNESS: single
          (D) TOPOLOGY: linear

    (ii) MOLECULE TYPE: peptide

    (vi) ORIGINAL SOURCE:
          (A) ORGANISM: FIGURE 9: IB-AMP2

    (xi) SEQUENCE DESCRIPTION: SEQ ID NO: 2:

Gly Arg Arg Cys Cys Asn Trp Gly Pro Gly Arg Arg Tyr Cys Lys Arg
1               5                   10                  15

Trp Cys


(2) INFORMATION FOR SEQ ID NO: 3:

     (i) SEQUENCE CHARACTERISTICS:
          (A) LENGTH: 11 amino acids
          (B) TYPE: amino acid
          (C) STRANDEDNESS: single
          (D) TOPOLOGY: linear

    (ii) MOLECULE TYPE: peptide

    (vi) ORIGINAL SOURCE:
          (A) ORGANISM: FIGURE 9: IB-AMP3

    (xi) SEQUENCE DESCRIPTION: SEQ ID NO: 3:

Gly Pro Gly Arg Lys Tyr Cys Lys Arg Trp Cys
1               5                   10


(2) INFORMATION FOR SEQ ID NO: 4:

     (i) SEQUENCE CHARACTERISTICS:
```

-continued (A) LENGTH: 18 amino acids
(B) TYPE: amino acid
(C) STRANDEDNESS: single
(D) TOPOLOGY: linear (ii) MOLECULE TYPE: peptide (vi) ORIGINAL SOURCE:
(A) ORGANISM: FIGURE 9: IB-AMP4

(xi) SEQUENCE DESCRIPTION: SEQ ID NO: 4:

```
Gly Arg Arg Cys Cys Gly Trp Gly Pro Gly Arg Arg Tyr Cys Arg Arg
1               5                   10                  15

Trp Cys
```

(2) INFORMATION FOR SEQ ID NO: 5:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 5:

```
Gly Pro Gly Arg Arg Tyr
1               5
```

(2) INFORMATION FOR SEQ ID NO: 6:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: IB-AMP1-C (xi) SEQUENCE DESCRIPTION: SEQ ID NO: 6:

```
GNTGTCTGTC CGNTGGGGNC C                                            21
```

(2) INFORMATION FOR SEQ ID NO: 7:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: IB-AMP1-B (xi) SEQUENCE DESCRIPTION: SEQ ID NO: 7:

```
CACCANCTGN ACGACAGATA                                              20
```

(2) INFORMATION FOR SEQ ID NO: 8:

(i) SEQUENCE CHARACTERISTICS:
(A) LENGTH: 1230 base pairs
(B) TYPE: nucleic acid
(C) STRANDEDNESS: single
(D) TOPOLOGY: linear (ii) MOLECULE TYPE: cDNA -continued (vi) ORIGINAL SOURCE:
(A) ORGANISM: FIGURE 10

(xi) SEQUENCE DESCRIPTION: SEQ ID NO: 8:

```
ATTTTTAGGT GAGGAAAAAT GGTCCAAAAA GGTGTAGTCT TTGGGGTGCT CCTAATTCTC     60

TTCATCTGCT CTACGCTCAC TTCGGCCGAT TCGAAGCCAA ACCCTACGAA AGAGGAAGAA    120

CCAGCGAAGA AACCGGATGA GGTCAGCGTA AAGAGCGGTG GACCGGAGGT GTCGGAGGAT    180

CAATACCGTC ATCGGTGCTG CGCTTGGGGA CCTGGGCGAA AATATTGCAA GCGGTGGTGT    240

GCTAACGCTG AAGAGGCGGC GGCCGCAATC CCCGAGGCAA GTGAAGAATT AGCTCAGGAG    300

GAGGCTCCGG TGTACTCGGA GGATCAGTGG GGTCGTCGGT GCTGCGGCTG GGGACCCGGC    360

CGAAGATACT GCGTGCGCTG GTGTCAAAAC GCGGAAGAGG CGGCCGCGGC AATCCCCGAG    420

GCGACTGAAA AAGCTCAGGA GGCTCCGGTG TACTCGGAGG ATCAGTGGGG TCGTCGATGC    480

TGCGGCTGGG GACCCGGCCG ACGGTATTGC GTGCGCTGGT GTCAAAACGC GGAAGAGGCG    540

GCCGCGGCGG TGGCAATCCC CGAGGCAAGT GAGAAAGCTC AGGAGGGACC CGTGTACTCG    600

GAGGATCAGT GGGGTCGCCG ATGCTGCGGT TGGGGACCTG GCCGTAGGTA TTGCGTGCGG    660

TGGTGCAGCA ACGCCGCCGA CGAGGTGGCA ACACCCGAGG ACGTAGAACC GGGTCAGTAC    720

GGTCGTCGGT GCTGCAACTG GGGACCTGGG CGAAGGTATT GCAAGCGGTG GTGTCATAAT    780

GCGGCTGAAG AGGCAACTCT CAAGGCATTT GAAGAGGAAG CAGCTCGGGA GCAACCGGTG    840

TACTCGGAGG ACCAGTGGGG TCGCCGGTGC TGCGGTTGGG GACCCGGCCG TAGGTACTGC    900

AGGCGGTGGT GTCAAAGCGC CGAAGAAGCG GCTGCGTTCC AGGCTGGGGA GGTAACTGCT    960

TCCTTGATGC TCATCATGTT TAAGGCATGC CCATGCATGG GGCCGGTGCC TTCTGTTTAA   1020

GGCCACTCTA GCTAGCTACG TACTCTTAAT AAGGGCACAT GAAAAAGTTT GTCCTTTAGA   1080

AATAAGGCAC AGTAAGAAAT AAAATGTCCA ACTTCTTTTA TGAAAGAAGT GAACAATAAG   1140

TGTAAGCTGA ATAATATATA TTGTGACACG TTTGTTGTTG TACAAAAATA ACATCTTTTC   1200

AGATGAACAA CCTTTAATGG AAAAAAAAAA                                    1230
```

(2) INFORMATION FOR SEQ ID NO: 9:

(i) SEQUENCE CHARACTERISTICS:
(A) LENGTH: 333 amino acids
(B) TYPE: amino acid
(C) STRANDEDNESS: single
(D) TOPOLOGY: linear (ii) MOLECULE TYPE: protein (vi) ORIGINAL SOURCE:
(A) ORGANISM: FIGURE 10

(xi) SEQUENCE DESCRIPTION: SEQ ID NO: 9:

```
Met Val Gln Lys Gly Val Val Phe Gly Val Leu Leu Ile Leu Phe Ile
1               5                   10                  15

Cys Ser Thr Leu Thr Ser Ala Asp Ser Lys Pro Asn Pro Thr Lys Glu
            20                  25                  30

Glu Glu Pro Ala Lys Lys Pro Asp Glu Val Ser Val Lys Ser Gly Gly
        35                  40                  45

Pro Glu Val Ser Glu Asp Gln Tyr Arg His Arg Cys Cys Ala Trp Gly
    50                  55                  60

Pro Gly Arg Lys Tyr Cys Lys Arg Trp Cys Ala Asn Ala Glu Glu Ala
65                  70                  75                  80
```

-continued

```
Ala Ala Ala Ile Pro Glu Ala Ser Glu Glu Leu Ala Gln Glu Glu Ala
                85                  90                  95

Pro Val Tyr Ser Glu Asp Gln Trp Gly Arg Arg Cys Cys Gly Trp Gly
            100                 105                 110

Pro Gly Arg Arg Tyr Cys Val Arg Trp Cys Gln Asn Ala Glu Glu Ala
        115                 120                 125

Ala Ala Ala Ile Pro Glu Ala Thr Glu Lys Ala Gln Glu Ala Pro Val
    130                 135                 140

Tyr Ser Glu Asp Gln Trp Gly Arg Arg Cys Cys Gly Trp Gly Pro Gly
145                 150                 155                 160

Arg Arg Tyr Cys Val Arg Trp Cys Gln Asn Ala Glu Glu Ala Ala Ala
                165                 170                 175

Ala Val Ala Ile Pro Glu Ala Ser Glu Lys Ala Gln Glu Gly Pro Val
            180                 185                 190

Tyr Ser Glu Asp Gln Trp Gly Arg Arg Cys Cys Gly Trp Gly Pro Gly
        195                 200                 205

Arg Arg Tyr Cys Val Arg Trp Cys Ser Asn Ala Ala Asp Glu Val Ala
    210                 215                 220

Thr Pro Glu Asp Val Glu Pro Gly Gln Tyr Gly Arg Arg Cys Cys Asn
225                 230                 235                 240

Trp Gly Pro Gly Arg Arg Tyr Cys Lys Arg Trp Cys His Asn Ala Ala
                245                 250                 255

Glu Glu Ala Thr Leu Lys Ala Phe Glu Glu Glu Ala Ala Arg Glu Gln
            260                 265                 270

Pro Val Tyr Ser Glu Asp Gln Trp Gly Arg Arg Cys Cys Gly Trp Gly
        275                 280                 285

Pro Gly Arg Arg Tyr Cys Arg Arg Trp Cys Gln Ser Ala Glu Glu Ala
    290                 295                 300

Ala Ala Phe Gln Ala Gly Glu Val Thr Ala Ser Leu Met Leu Ile Met
305                 310                 315                 320

Phe Lys Ala Cys Pro Cys Met Gly Pro Val Pro Ser Val
                325                 330
```

(2) INFORMATION FOR SEQ ID NO: 10:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (vi) ORIGINAL SOURCE:
(A) ORGANISM: IB-AMP1

(xi) SEQUENCE DESCRIPTION: SEQ ID NO: 10:

```
Gln Trp Gly Arg Arg Cys Cys Gly Trp Gly Pro Gly Arg Arg Tyr Cys
1               5                   10                  15

Val Arg Trp Cys
            20
```

(2) INFORMATION FOR SEQ ID NO: 11:

(i) SEQUENCE CHARACTERISTICS:
(A) LENGTH: 20 amino acids
(B) TYPE: amino acid
(C) STRANDEDNESS: single
(D) TOPOLOGY: linear -continued (ii) MOLECULE TYPE: peptide (vi) ORIGINAL SOURCE:
(A) ORGANISM: IB-AMP2

(xi) SEQUENCE DESCRIPTION: SEQ ID NO: 11:

```
Gln Tyr Gly Arg Arg Cys Cys Asn Trp Gly Pro Gly Arg Arg Tyr Cys
1               5                   10                  15

Lys Arg Trp Cys
            20
```

(2) INFORMATION FOR SEQ ID NO: 12:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (vi) ORIGINAL SOURCE:
(A) ORGANISM: IB-AMP3

(xi) SEQUENCE DESCRIPTION: SEQ ID NO: 12:

```
Gln Tyr Arg His Arg Cys Cys Ala Trp Gly Pro Gly Arg Lys Tyr Cys
1               5                   10                  15

Lys Arg Trp Cys
            20
```

(2) INFORMATION FOR SEQ ID NO: 13:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (vi) ORIGINAL SOURCE:
(A) ORGANISM: IB-AMP4

(xi) SEQUENCE DESCRIPTION: SEQ ID NO: 13:

```
Gln Trp Gly Arg Arg Cys Cys Gly Trp Gly Pro Gly Arg Arg Tyr Cys
1               5                   10                  15

Arg Arg Trp Cys
            20
```

(2) INFORMATION FOR SEQ ID NO: 14:

(i) SEQUENCE CHARACTERISTICS:
(A) LENGTH: 28 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 14:

```
Ala Asn Ala Glu Glu Ala Ala Ala Ala Ile Pro Glu Ala Ser Glu Glu
1               5                   10                  15

Leu Ala Gln Glu Glu Ala Pro Val Tyr Ser Glu Asp
            20                  25
```

(2) INFORMATION FOR SEQ ID NO: 15:

-continued (i) SEQUENCE CHARACTERISTICS:
(A) LENGTH: 26 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 15:

```
Gln Asn Ala Glu Glu Ala Ala Ala Ala Ile Pro Glu Ala Thr Glu Lys
1               5                   10                  15

Ala Gln Glu Ala Pro Val Tyr Ser Glu Asp
            20                  25
```

(2) INFORMATION FOR SEQ ID NO: 16:

(i) SEQUENCE CHARACTERISTICS:
(A) LENGTH: 28 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 16:

```
Gln Asn Ala Glu Glu Ala Ala Ala Ala Val Ala Ile Pro Glu Ala Ser
1               5                   10                  15

Glu Lys Ala Gln Glu Gly Pro Val Tyr Ser Glu Asp
            20                  25
```

(2) INFORMATION FOR SEQ ID NO: 17:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 17:

```
Ser Asn Ala Ala Asp Glu Val Ala Thr Pro Glu Asp Val Glu Pro Gly
1               5                   10                  15
```

(2) INFORMATION FOR SEQ ID NO: 18:

(i) SEQUENCE CHARACTERISTICS:
(A) LENGTH: 26 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 18:

```
His Asn Ala Ala Glu Glu Ala Thr Leu Lys Ala Phe Glu Glu Glu Ala
1               5                   10                  15

Ala Arg Glu Gln Pro Val Tyr Ser Glu Asp
            20                  25
```

(2) INFORMATION FOR SEQ ID NO: 19:

(i) SEQUENCE CHARACTERISTICS:
(A) LENGTH: 29 amino acids
(B) TYPE: amino acid
(C) STRANDEDNESS: single
(D) TOPOLOGY: linear -continued

```
    (ii) MOLECULE TYPE: peptide

    (xi) SEQUENCE DESCRIPTION: SEQ ID NO: 19:

Lys Pro Asn Pro Thr Lys Glu Glu Glu Pro Ala Lys Lys Pro Asp Glu
1               5                   10                  15

Val Ser Val Lys Ser Gly Gly Pro Glu Val Ser Glu Asp
            20                  25


(2) INFORMATION FOR SEQ ID NO: 20:

     (i) SEQUENCE CHARACTERISTICS:
          (A) LENGTH: 35 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO: 20:

Gln Ser Ala Glu Glu Ala Ala Ala Phe Gln Ala Gly Glu Val Thr Ala
1               5                   10                  15

Ser Leu Met Leu Ile Met Phe Lys Ala Cys Pro Cys Met Gly Pro Val
            20                  25                  30

Pro Ser Val
        35


(2) INFORMATION FOR SEQ ID NO: 21:

     (i) SEQUENCE CHARACTERISTICS:
          (A) LENGTH: 25 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO: 21:

Met Val Gln Lys Gly Val Val Phe Gly Val Leu Leu Ile Leu Phe Ile
1               5                   10                  15

Cys Ser Thr Leu Thr Ser Ala Asp Ser
            20                  25
```